US011612417B2

(12) United States Patent
Jones et al.

(10) Patent No.: US 11,612,417 B2
(45) Date of Patent: Mar. 28, 2023

(54) SPINAL FIXATION SYSTEM

(71) Applicant: K2M, Inc., Leesburg, VA (US)

(72) Inventors: Scott A. Jones, Mcmurray, PA (US);
Oheneba Boachie-Adjei, Garden City, NY (US); Larry E. McClintock, Gore, VA (US); Kevin Strauss, Atlanta, GA (US); John Carbone, Lutherville, MD (US)

(73) Assignee: K2M, Inc., Leesburg, VA (US)

( * ) Notice: Subject to any disclaimer, the term of this patent is extended or adjusted under 35 U.S.C. 154(b) by 641 days.

(21) Appl. No.: 16/686,703

(22) Filed: Nov. 18, 2019

(65) Prior Publication Data
US 2020/0170680 A1 Jun. 4, 2020

Related U.S. Application Data

(60) Continuation of application No. 15/905,012, filed on Feb. 26, 2018, now Pat. No. 10,499,957, which is a
(Continued)

(51) Int. Cl.
*A61B 17/70* (2006.01)
*A61B 17/86* (2006.01)
*A61B 17/00* (2006.01)

(52) U.S. Cl.
CPC ...... *A61B 17/7037* (2013.01); *A61B 17/7086* (2013.01); *A61B 17/8625* (2013.01); *A61B 2017/0046* (2013.01)

(58) Field of Classification Search
CPC ............ A61B 17/7037; A61B 17/7086; A61B 17/8625; A61B 2017/0046
(Continued)

(56) References Cited

U.S. PATENT DOCUMENTS 5,116,336 A 5/1992 Frigg
5,360,431 A 11/1994 Puno et al.
(Continued)

FOREIGN PATENT DOCUMENTS

EP 1634537 A1 3/2006
EP 1774919 A1 4/2007
(Continued)

OTHER PUBLICATIONS

Amy W. L. Kwok, et al.; Insertional Torque and Pull-out Strengths of Conical and Cylindrical Pedicle Screws in Cadaveric Bone, Spine, 1996, vol. 21, No. 21, pp. 2429-2434.
(Continued)

*Primary Examiner* — Eduardo C Robert
*Assistant Examiner* — David C Comstock
(74) *Attorney, Agent, or Firm* — Lerner, David, Littenberg, Krumholz & Mentlik, LLP

(57) ABSTRACT

A polyaxial pedicle screw includes a housing, a bone screw member, and an anvil. The bone screw member includes a head and a threaded shaft extending from the head. The head is selectively securable within the housing. The anvil is positionable within the housing adjacent to the head of the bone screw member when the anvil and the head of the bone screw member are positioned within the housing. The anvil may define one or more grooves in an outer surface of the anvil. The groove defines a flap that is flexibly attached to the anvil to enable the anvil to flex an amount sufficient to maintain the head of the bone screw in constant contact with the anvil when the bone screw member is moved relative to the anvil. A rod reducer may be secured to the polyaxial pedicle screw to secure a spinal rod within the housing.

18 Claims, 28 Drawing Sheets

Related U.S. Application Data continuation of application No. 15/210,448, filed on Jul. 14, 2016, now Pat. No. 9,924,973, which is a division of application No. 13/595,533, filed on Aug. 27, 2012, now Pat. No. 9,393,049, which is a continuation-in-part of application No. 13/214,331, filed on Aug. 22, 2011, now Pat. No. 8,882,817.

(60) Provisional application No. 61/527,632, filed on Aug. 26, 2011, provisional application No. 61/375,354, filed on Aug. 20, 2010.

(58) Field of Classification Search
USPC .............................. 606/266–272, 305, 308
See application file for complete search history.

(56) References Cited

U.S. PATENT DOCUMENTS

| | | |
|---|---|---|
| 5,443,467 A | 8/1995 | Biedermann et al. |
| 5,443,509 A | 8/1995 | Boucher et al. |
| 5,466,237 A | 11/1995 | Byrd, III et al. |
| 5,474,555 A | 12/1995 | Puno et al. |
| 5,476,464 A | 12/1995 | Metz-Stavenhagen et al. |
| 5,549,608 A | 8/1996 | Errico et al. |
| 5,554,157 A | 9/1996 | Errico et al. |
| 5,584,834 A | 12/1996 | Errico et al. |
| 5,586,984 A | 12/1996 | Errico et al. |
| 5,647,873 A | 7/1997 | Errico et al. |
| 5,669,911 A | 9/1997 | Errico et al. |
| 5,672,176 A | 9/1997 | Biedermann et al. |
| 5,690,630 A | 11/1997 | Errico et al. |
| 5,733,285 A | 3/1998 | Errico et al. |
| 5,733,286 A | 3/1998 | Errico et al. |
| 5,797,911 A | 8/1998 | Sherman et al. |
| 5,817,094 A | 10/1998 | Errico et al. |
| 5,863,293 A | 1/1999 | Richelsoph |
| 5,885,286 A | 3/1999 | Sherman et al. |
| 5,964,760 A | 10/1999 | Richelsoph |
| 6,010,503 A | 1/2000 | Richelsoph et al. |
| 6,074,391 A | 6/2000 | Metz-Stavenhagen et al. |
| 6,090,110 A | 7/2000 | Metz-Stavenhagen |
| 6,261,287 B1 | 7/2001 | Metz-Stavenhagen |
| 6,273,888 B1 | 8/2001 | Justis |
| 6,280,442 B1 | 8/2001 | Barker et al. |
| 6,296,642 B1 | 10/2001 | Morrison et al. |
| 6,355,040 B1 | 3/2002 | Richelsoph et al. |
| RE37,665 E | 4/2002 | Ralph et al. |
| 6,485,491 B1 | 11/2002 | Farris et al. |
| 6,537,276 B2 | 3/2003 | Metz-Stavenhagen |
| 6,726,689 B2 | 4/2004 | Jackson |
| 6,869,433 B2 | 3/2005 | Glascott |
| RE39,089 E | 5/2006 | Ralph et al. |
| 7,087,057 B2 | 8/2006 | Konieczynski et al. |
| 7,128,743 B2 | 10/2006 | Metz-Stavenhagen |
| 7,211,086 B2 | 5/2007 | Biedermann et al. |
| 7,223,268 B2 | 5/2007 | Biedermann |
| 7,591,839 B2 | 9/2009 | Biedermann et al. |
| 7,695,497 B2 | 4/2010 | Cordaro et al. |
| 7,749,258 B2 | 7/2010 | Biedermann et al. |
| 7,867,258 B2 | 1/2011 | Drewry et al. |
| 7,947,065 B2 | 5/2011 | Hammill, Sr. et al. |
| 7,951,172 B2 | 5/2011 | Chao et al. |
| 8,012,188 B2 | 9/2011 | Melkent et al. |
| 8,403,971 B2 | 3/2013 | Barrus et al. |
| 8,430,914 B2 | 4/2013 | Spratt et al. |
| 8,506,601 B2 | 8/2013 | Gephart et al. |
| 8,556,938 B2 | 10/2013 | Jackson et al. |
| 8,814,919 B2 | 8/2014 | Barrus et al. |
| 8,882,817 B2 | 11/2014 | Jones et al. |
| 9,393,049 B2 | 7/2016 | Jones et al. |
| 9,451,993 B2 | 9/2016 | Jackson |
| 9,453,526 B2 | 9/2016 | Black et al. |
| 9,924,971 B2 | 3/2018 | Biedermann et al. |
| 9,924,973 B2 * | 3/2018 | Jones ............... A61B 17/7037 |
| 10,499,957 B2 * | 12/2019 | Jones ............... A61B 17/7086 |
| 10,716,609 B2 | 7/2020 | Biedermann et al. |
| 2002/0026193 A1 | 2/2002 | Barker et al. |
| 2003/0004512 A1 | 1/2003 | Farris et al. |
| 2003/0125741 A1 | 7/2003 | Biedermann et al. |
| 2005/0192571 A1 | 9/2005 | Abdelgany |
| 2005/0277928 A1 * | 12/2005 | Boschert ............ A61B 17/7037 606/328 |
| 2006/0074419 A1 | 4/2006 | Taylor et al. |
| 2006/0111715 A1 | 5/2006 | Jackson |
| 2006/0200131 A1 | 9/2006 | Chao et al. |
| 2008/0091213 A1 | 4/2008 | Jackson |
| 2008/0125816 A1 | 5/2008 | Jackson |
| 2008/0312701 A1 | 12/2008 | Butters et al. |
| 2009/0005814 A1 | 1/2009 | Miller et al. |
| 2009/0163956 A1 | 6/2009 | Biedermann et al. |
| 2009/0228053 A1 | 9/2009 | Kolb et al. |
| 2009/0264941 A1 | 10/2009 | Banouskou |
| 2010/0114171 A1 | 5/2010 | Boachie-Adjei et al. |
| 2010/0160977 A1 | 6/2010 | Gephart et al. |
| 2010/0160978 A1 | 6/2010 | Carbone |
| 2010/0204735 A1 * | 8/2010 | Gephart ............ A61B 17/7082 606/279 |
| 2011/0040336 A1 | 2/2011 | Hammill et al. |

FOREIGN PATENT DOCUMENTS

| | | |
|---|---|---|
| EP | 2052690 A1 | 4/2009 |
| JP | 2004508130 A | 3/2004 |
| JP | 2007526007 A | 9/2007 |
| JP | 2009142655 A | 7/2009 |
| WO | 2009015100 A2 | 1/2009 |
| WO | 2010077284 A1 | 7/2010 |

OTHER PUBLICATIONS

Ferris M. Pfeiffer et al.; Comparison of Pullout Strength for Pedicle Screws of Different Designs, Spine, 2006, vol. 31, No. 23, 2006, pp. E867-E870.

International Search Report and Written Opinion of the International Searching Authority dated Mar. 5, 2011 from counterpart International Application No. PCT/US2011/048573.

J.R. Chapman et al.; Factors Affecting the Pullout Strength of Cancellous Bone Screws, Journal of Biomechanical Engineering, Aug. 1996, vol. 118, pp. 391-398.

Japanese Office Action dated Feb. 28, 2017 in corresponding Japanese Patent Application No. 2016-097141 with English translation, 14 pages.

Japanese Office Action dated Jun. 2, 2015 in corresponding JP Application 2013-525009.

Japanese Office Action dated Jun. 20, 2017 for application No. 2013-525009.

JP Office Action dated Jan. 19, 2016 in corresponding JP Patent Application No. 2013-525009, together with English-language translation, 6 pages.

Oberg, E.; Jones, F.D.; Horton, H.L.; Ryffell, H.; Machinery's Handbook, 2000, Industrial Press, 26.sup.th Edition, pp. 1584-1591.

Robert F. McLain et al.; Lumbar Pedicle Screw Salvage: Pullout Testing of Three Different Pedicle Screw Designs; Journal of Spinal Disorders, 1995, vol. 8, No. 1, pp. 62-68.

Standard Specification and Test Methods for Metallic Medical Bone Screws; ASTM F543-07, ASTM International, 2007; pp. 1-20; www.astm.org.

Titanium Versalok Polyaxial Screw, Wright Medical Technology Inc., Apr. 1997; 1 page.

* cited by examiner

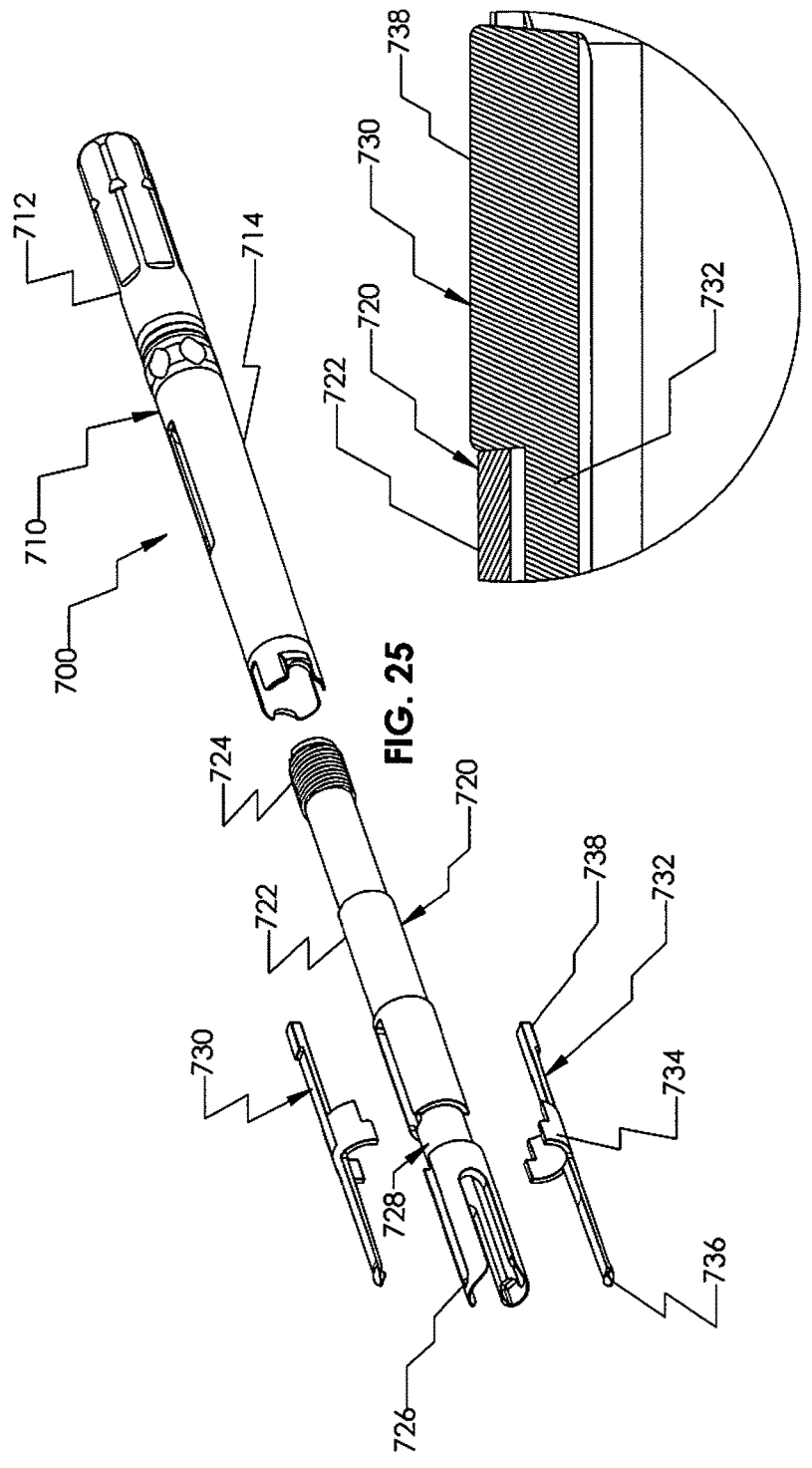
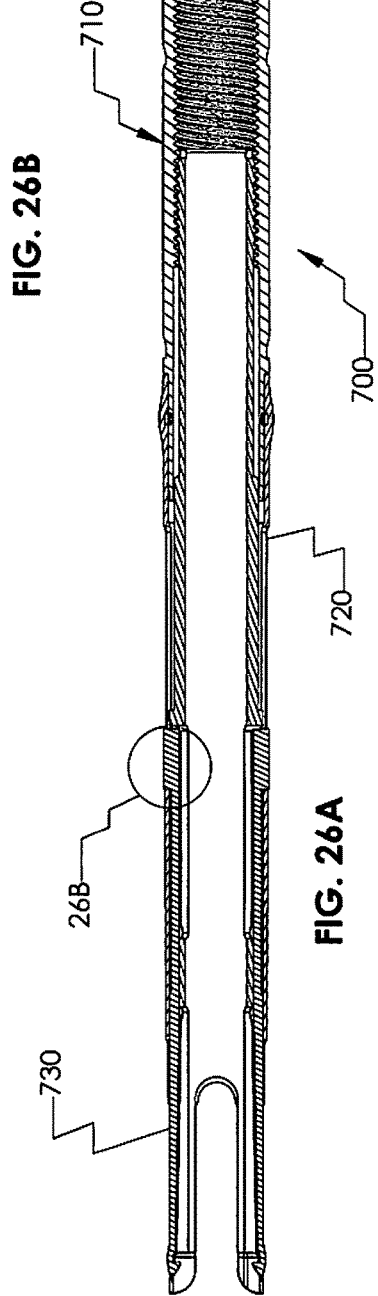
FIG. 25
FIG. 26B
FIG. 26A

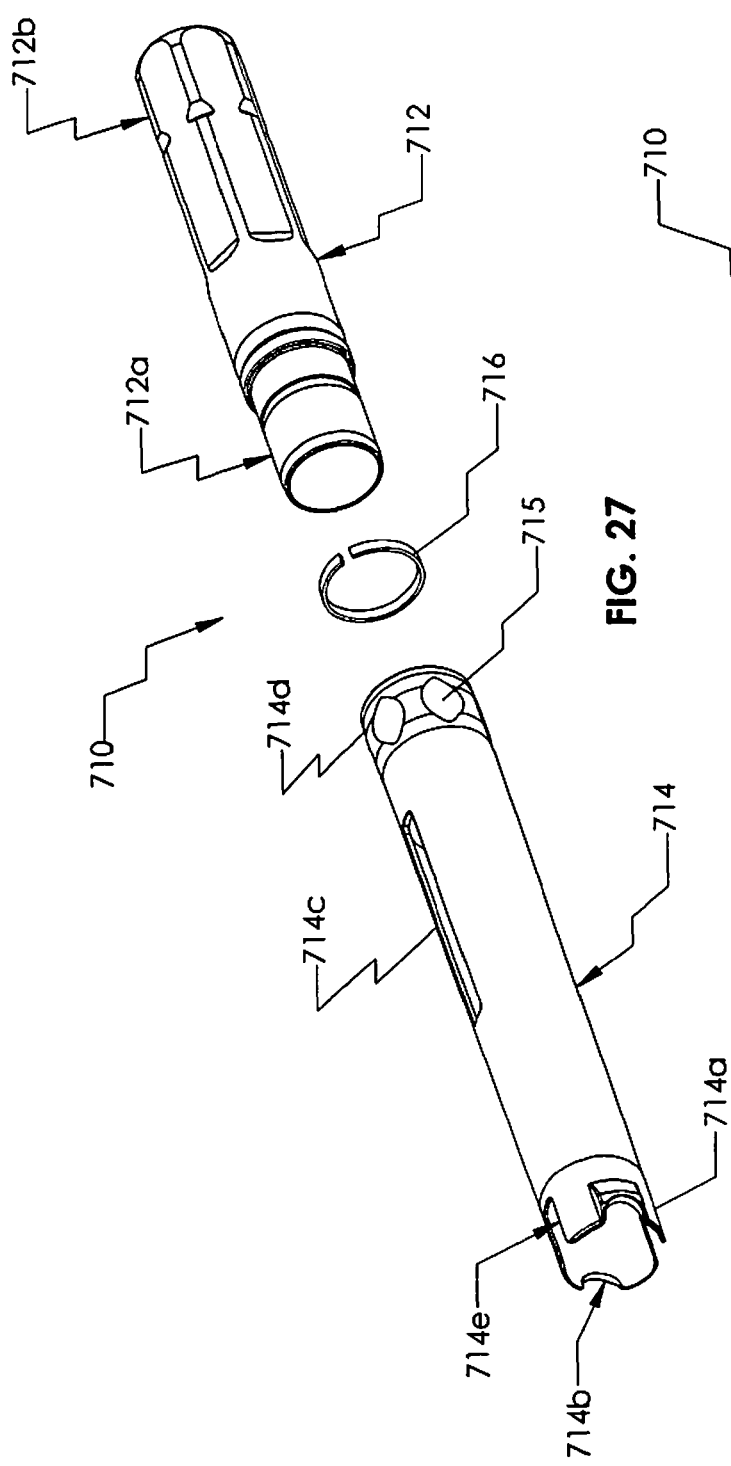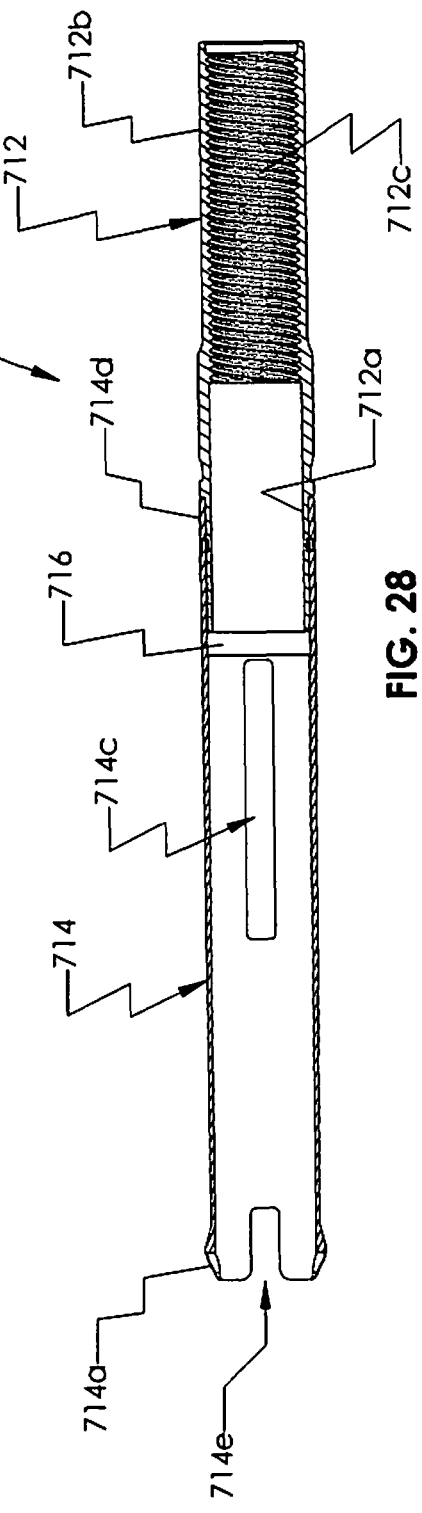

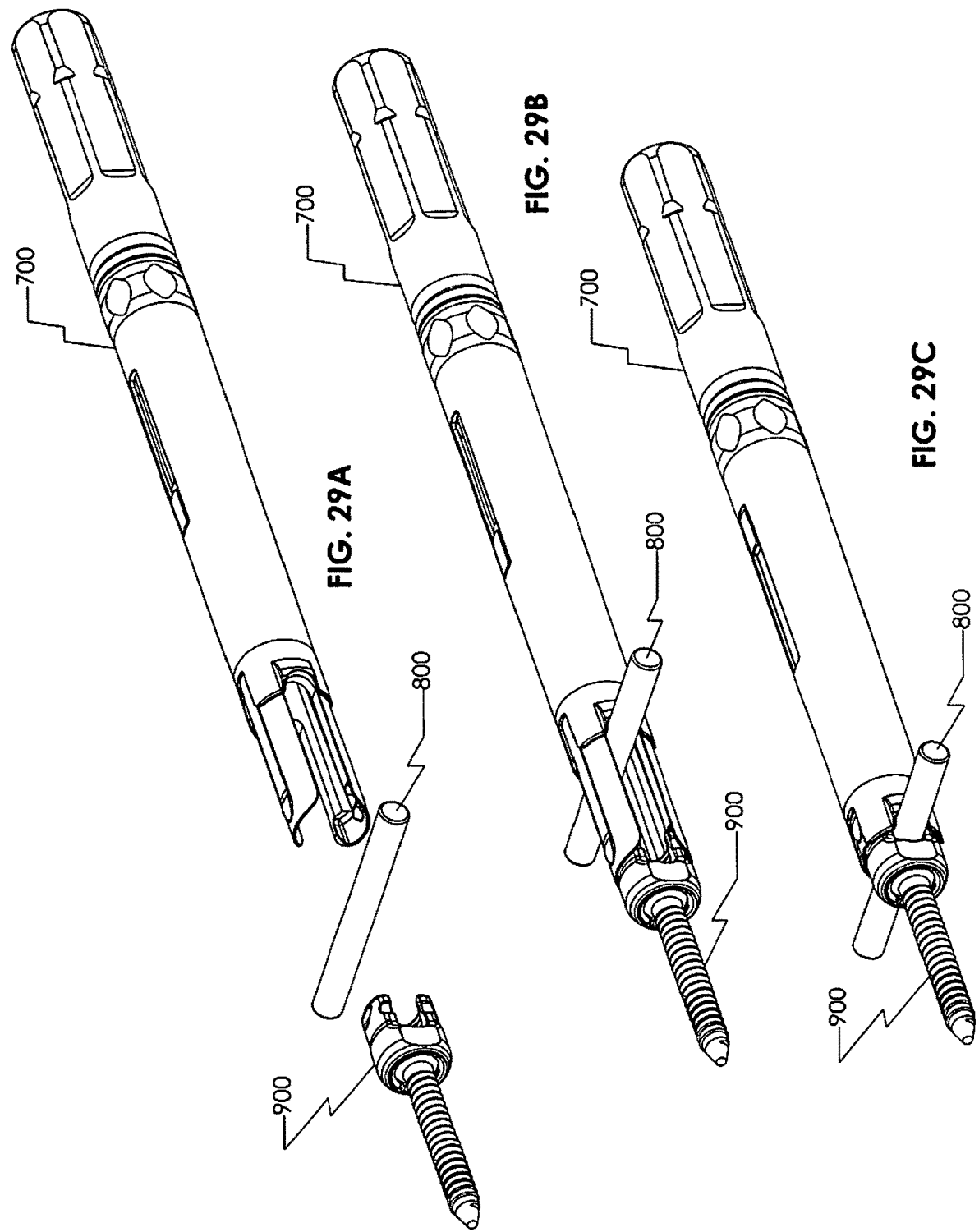

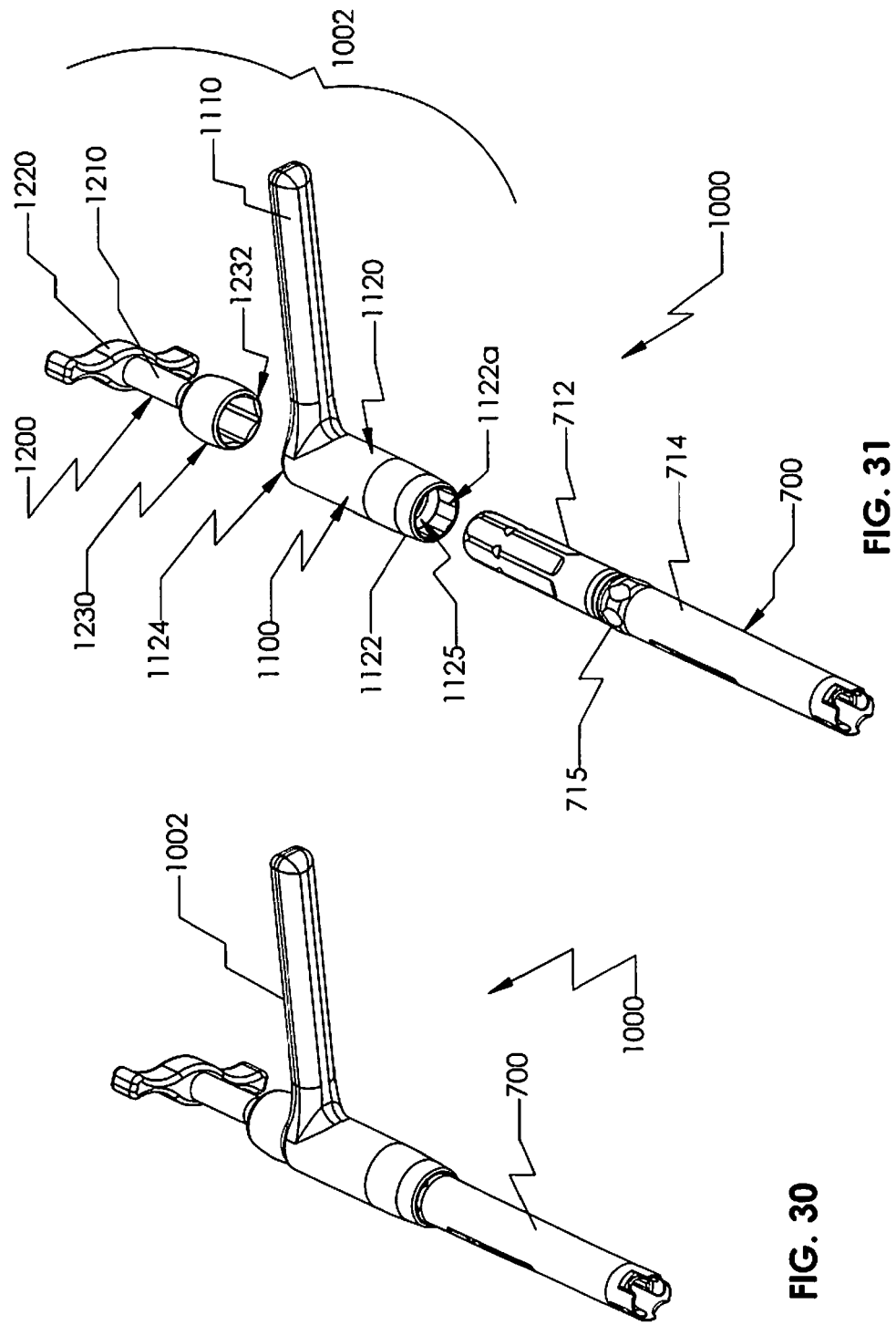

SPINAL FIXATION SYSTEM

CROSS REFERENCE TO RELATED APPLICATIONS

This application is a continuation of U.S. patent application Ser. No. 15/905,012, filed on Feb. 6, 2018, which is a continuation of U.S. patent application Ser. No. 15/210,448, filed on Jul. 14, 2016, which is a divisional of U.S. patent application Ser. No. 13/595,533, filed on Aug. 27, 2012, now U.S. Pat. No. 9,393,049, which is a continuation-in-part of U.S. patent application Ser. No. 13/214,331, filed on Aug. 22, 2011, now U.S. Pat. No. 8,882,817, which claims priority to, and the benefit of, U.S. Provisional Patent Application No. 61/375,354, filed on Aug. 20, 2010. The present application also claims priority to, and the benefit of, U.S. Provisional Patent Application No. 61/527,632, filed on Aug. 26, 2011. The entire contents of each of these prior applications are incorporated by reference herein.

BACKGROUND

Technical Field

The present disclosure relates generally to orthopedic surgery with particular regard to spinal surgery. Specifically, the present disclosure relates to spinal fixation systems.

Description of Related Art

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include, PEEK interbody spacers, metal cages and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. The opposing pair of longitudinally linked rods is commonly disposed along the long axis of the spine via a posterior approach. Pedicle screws can be manufactured from any biocompatible material, including cobalt chrome, stainless steel, titanium and PEEK (polyetheretherketone).

To meet the problem of providing a rigid pedicle screw and rod construct, especially for addressing the demands of stiff deformity corrections, larger rod constructs have been made to improve the strength of the screw and rod construct. Spinal rods are typically made of titanium alloy. However, when large deformity corrections are necessary these rods are not always strong enough. Larger diameter stainless steel rods have been made for these applications, but a larger rod requires a larger mating screw head to contain the rod, which, in turn, increases the profile of the construct. In addition, in order to reduce the likelihood of material incompatibility in vivo, the screw assembly also needs to be made of stainless steel to match the rod material, which is not a cost effective alternative.

Therefore, a need exists for a cost effective, rigid screw and rod construct that can still maintain large, stiff deformity corrections.

SUMMARY

The present disclosure is directed to a polyaxial pedicle screw including a housing, a bone screw member, and an anvil. The bone screw member is selectively positionable at a plurality of angles relative to the housing when engaged to the housing and securable relative to the housing at a cone angle of up to approximately 80 degrees. The bone screw member includes a head and a threaded shaft extending from the head. The head is selectively securable within the housing. The head may include surface texture that frictionally engages with the anvil such that a user applied force is necessary to reposition the bone screw member relative to the anvil when the bone screw member is disposed in engagement with the anvil. The head of the bone screw member includes a first ponion and a second portion. Only one of the first and second ponions enable the head to fit through an opening defined in the housing and the other of the first and second portions maintains the head of the bone screw member within the housing once inserted. One of the first and second portions may be cylindrically shaped and the other of the first and second portions may be spherically shaped. The cylindrically shaped portion enables the head to fit through the opening in the housing in an insertion orientation of the screw head relative to the housing, and the spherically shaped portion maintains the head of the bone screw member within the housing once inserted and moved away from the insertion orientation.

The anvil is positionable within the housing adjacent to the head of the bone screw member when the anvil and the head of the bone screw member are positioned within the housing. A set screw is positionable within the housing to secure a rod member within the housing adjacent the anvil.

The anvil may define one or more grooves in an outer surface of the anvil. The groove defines one or more flaps. The one or more flaps are flexibly attached to the anvil to enable the anvil to flex an amount sufficient to maintain the head of the bone screw member in constant frictional contact with the anvil when the bone screw member is moved relative to the anvil. The anvil may define a cavity having a surface with a plurality of radii of curvature to accommodate rod members of variously sized diameters. The surface of the cavity may define a first section with a first radius of curvature, a second section with a second radius of curvature, and a third section with a third radius of curvature. In this respect, the plurality of radii of curvature defines a compound curve that provides two or more lines of contact on a plurality of different diameter rod members.

The outer surface of the anvil may have a non-round shape to prevent disorientation of the anvil when positioning the rod member adjacent the anvil. The anvil may include a protuberance on the outer surface of the anvil and the housing may define a slot on an inner surface of the housing. The protuberance and the slot may be engagable to maintain the alignment of the anvil with respect to the housing.

A compression ring or cap may be securable to the housing to prevent the bone screw member from re-orienting to a position in which the cylindrically shaped portion of the screw head is aligned with the housing opening. The housing may include a collar extending therefrom. The collar may define a cut out to facilitate the positioning of the head within the housing. The compression ring or cap is securable (such as by friction fit, gluing, welding or the like) to the collar to cover the cut out after the head of the bone screw member is positioned within the housing.

According to one aspect, a polyaxial pedicle screw includes a bone screw member, a housing, one or more wedge members, and one or more pins. The housing is positionable on the head of the bone screw member and defines one or more pin channels therethrough. One or more wedge members are position able within the housing adjacent the head to facilitate the securement of the head of the bone screw member and a rod member within the housing. A set screw is threadably engagable with an inner surface of the housing to secure a rod member adjacent the wedge member.

The one or more wedge members define one or more pin pockets in an outer surface thereof. The one or more pins are positionable within the one or more pin channels. The one or more pin pockets maintain the one or more wedge members within the housing. The bone screw member is selectively positionable at a plurality of angles relative to the housing when engaged to the housing and securable relative to the housing at a cone angle of up to approximately 80 degrees. The bone screw member has a threaded shaft and a head. The head of the bone screw member includes a first portion and a second portion. Only one of the first and second portions enable the head to fit through an opening defined in the housing and the other of the first and second portions maintains the head of the bone screw member within the housing once inserted. One of the first and second portions is cylindrically shaped and the other of the first and second portions is spherically shaped. The cylindrically shaped portion enables the head to fit through the opening in the housing. The spherically shaped portion maintains the head of the bone screw member within the housing once inserted.

The polyaxial pedicle screw may include a first wedge member and a second wedge member. Each of the first and second wedge members are positionable adjacent the head of the bone screw member. The first wedge member and the second wedge member define a cavity having a surface with a plurality of radii of curvature to accommodate variously sized rod members. The surface of the cavity defines a first section with a first radius of curvature, a second section with a second radius of curvature, and a third section with a third radius of curvature.

A compression ring or cap may be securable to the housing to prevent the bone screw member from re-orienting to a position in which the cylindrically shaped portion of the head of the bone screw member is aligned with the housing opening.

According to one aspect, a polyaxial pedicle screw includes a bone screw member and a housing. The bone screw member includes a head having a threaded shaft extending from the head. The housing is position able on the head of the bone screw and has a distal opening. The bone screw member is position able at a plurality of angles relative to the housing when engaged to the housing and securable relative to the housing at angles within a cone angle of up to approximately 80 degrees. A set screw is positionable within the housing to secure a rod member within the housing adjacent the anvil.

The head includes a first portion and a second portion. The first head portion is configured and dimensioned to pass through the housing distal opening and the second head portion is configured and dimensioned not to pass through the housing distal opening. The first head portion may include a substantially cylindrically shaped section. The cylindrically shaped section defines a diameter that is less than the diameter of the housing distal opening. The second portion of the head may define a diameter larger than the diameter of the housing distal opening. The second portion of the head may include a substantially spherical section.

The housing may further define a collar extending from the distal end of the housing. The collar may define a cut out section. As can be appreciated, the screw assumes an insertion position with the neck of the screw disposed in the cut out section with the cylindrically shaped section of the head aligned with the housing distal opening.

An anvil is positionable within the housing adjacent to the head of the bone screw member when the anvil and the head of the bone screw member are positioned within the housing. The anvil defines one or more grooves in an outer surface of the anvil. The groove defines one or more flaps. The one or more flaps are flexibly attached to the anvil to enable the anvil to flex an amount sufficient to maintain the head of the bone screw member in constant contact with the anvil. The anvil defines a cavity having a surface with a plurality of radii of curvature to accommodate variously sized rod members. The surface of the cavity defines a first section with a first radius of curvature, a second section with a second radius of curvature, and a third section with a third radius of curvature such that the plurality of radii of curvature defines a compound curve that provides two or more lines of contact on a plurality of different diameter rod members. The outer surface of the anvil may have a non-round shape to prevent disorientation of the anvil when positioning a rod member adjacent the anvil. The anvil may include a protuberance on the outer surface of the anvil and the housing may define a slot on an inner surface of the housing. The protuberance and the slot are engagable to maintain the alignment of the anvil with respect to the housing.

The head of the bone screw member may include surface texture that frictionally engages with the anvil such that a user applied force is necessary to reposition the bone screw member relative to the anvil when the bone screw member is disposed in engagement with the anvil without a rod in the housing.

A cap is securable to the housing to prevent the bone screw member from re-orienting to a position in which the screw head first portion is aligned with the housing distal opening.

According to yet another aspect, the present disclosure is directed to a method of assembling a pedicle screw. The method includes providing a pedicle screw including a bone screw member and a housing. The bone screw member includes a head having a threaded shaft extending from the head. The head includes a first portion and a second portion. The housing is positionable on the head of the bone screw and has a distal opening. The first head portion is configured and dimensioned to pass through the housing distal opening and the second head portion is configured and dimensioned not to pass through the housing distal opening. The method involves the steps of positioning the screw relative to the housing such that the first housing portion is aligned with the housing distal opening, inserting the screw head through the housing distal opening with the first head portion aligned with the distal opening, and rotating the screw relative to the housing such that the first head portion is no longer aligned with the housing distal opening and the second head portion prevents the screw head from exiting through the distal opening.

One step of the method includes mounting a collar onto the housing with the screw head disposed in the housing to prevent the screw from reassuming the position with the cylindrically shaped section aligned with the housing distal opening.

According to one aspect, a system for securing a spinal rod to a pedicle screw includes a spinal rod, a polyaxial pedicle screw, a rod reducer, and a handle assembly.

The polyaxial pedicle screw includes a housing and a bone screw member. The bone screw member is configured for engagement with bone and is selectively movable relative to housing. The housing includes a saddle configured to receive the spinal rod. The rod reducer includes a proximal end and a distal end and defines a longitudinal axis between the proximal and distal ends. The rod reducer includes an outer member and an inner member. The inner member is selectively attachable to the housing of the polyaxial pedicle screw. The outer member is axially movable relative to the inner member when the inner member is secured to the housing of the polyaxial pedicle screw to secure the spinal rod within the saddle of the housing of the polyaxial pedicle screw. The outer member includes a proximal segment and a distal segment. The proximal segment is rotatable to axially translate the distal segment. The distal segment is engageable with the spinal rod to secure the spinal rod within the saddle upon the axial translation of the distal segment. The proximal segment independently rotates relative to the distal segment. The rod reducer includes a pair of gripping members configured to engage the housing of the polyaxial pedicle screw. The pair of gripping members is positioned between the inner and outer members of the rod reducer.

The handle assembly is selectively engageable with the rod reducer to move the outer member of the rod reducer axially relative to the inner member of the rod reducer. The handle assembly is configured to rotate the outer member so that the rotational movement of the outer member axially moves the outer member relative to the inner member. The handle assembly includes a turning handle and an anti-torque handle. The anti-torque handle is selectively engageable with the proximal end of the rod reducer and the turning handle is selectively engageable with a proximal end of the ant-torque handle.

According to another aspect, a method for securing a spinal rod to a pedicle screw includes providing a polyaxial pedicle screw including a housing and a bone screw member. The method includes the steps of securing the polyaxial pedicle screw within bone, securing a rod reducer to the polyaxial pedicle screw, the rod reducer including an inner member and an outer member, securing an independent handle assembly to the outer member of the rod reducer, rotating the outer member about the inner member with the independent handle assembly to axially advance the outer member relative to the inner member, approximating a spinal rod and the polyaxial pedicle screw as the outer member is advanced distally relative to the inner member, and securing the spinal rod to the polyaxial pedicle screw. The method may involve operatively coupling a turning handle and an anti-torque handle to the outer member. The method may include rotating the proximal segment independently of the distal segment to axially advance the distal segment of the outer member relative to the inner member where the outer member includes a proximal segment and a distal segment.

According to yet another aspect, a polyaxial pedicle screw includes a housing and a bone screw member. An anvil is positionable within the housing adjacent to the head of the bone screw member.

The bone screw member has a head supported within the housing and a shaft that extends from the housing. The shaft defines a longitudinal axis between leading and trailing ends of the shaft. The shaft is selectively movable relative to housing and includes a buttress thread form with a pressure flank portion that is nearly perpendicular to the longitudinal axis of the shaft to maximize load resistance of the pressure flank portion. The leading end of shaft may be tapered such that the buttress thread form tapers along a length of the tapered leading end. The length of the tapered leading end of the shaft may be approximately ⅓ of a length of the shaft. The pressure flank portion of the buttress thread form may be positioned at an angle offset from a perpendicular orientation relative to the longitudinal axis of the shaft by an amount ranging between approximately 1 and 5 degrees. The buttress thread form of the shaft may be a double lead thread.

BRIEF DESCRIPTION OF THE DRAWINGS

The above and other aspects and features of the present disclosure will become more apparent in light of the following detailed description when taken in conjunction with the accompanying drawings in which:

FIG. 25 is a perspective view, with parts separated, of a rod reducer in accordance with the present disclosure;

FIG. 26A is a cross-sectional view of the rod reducer of FIG. 25;

FIG. 26B is an enlarged cross-sectional view of the indicated area of detail shown in FIG. 26A;

FIG. 27 is a perspective view, with parts separated, of an outer member of the rod reducer shown in FIG. 25;

FIG. 28 is a cross-sectional view of the outer member of FIG. 27;

FIGS. 29A-29C are progressive perspective views illustrating a reduction of a rod into an embodiment of the presently disclosed pedicle screw with the rod reducer shown in FIG. 25;

FIG. 30 is a perspective view of a handle and rod reducer assembly in accordance with the present disclosure; and FIG. 31 is a perspective view, with parts separated, of the handle and rod reducer assembly of FIG. 30.

DETAILED DESCRIPTION OF THE EMBODIMENTS

Figure 1:
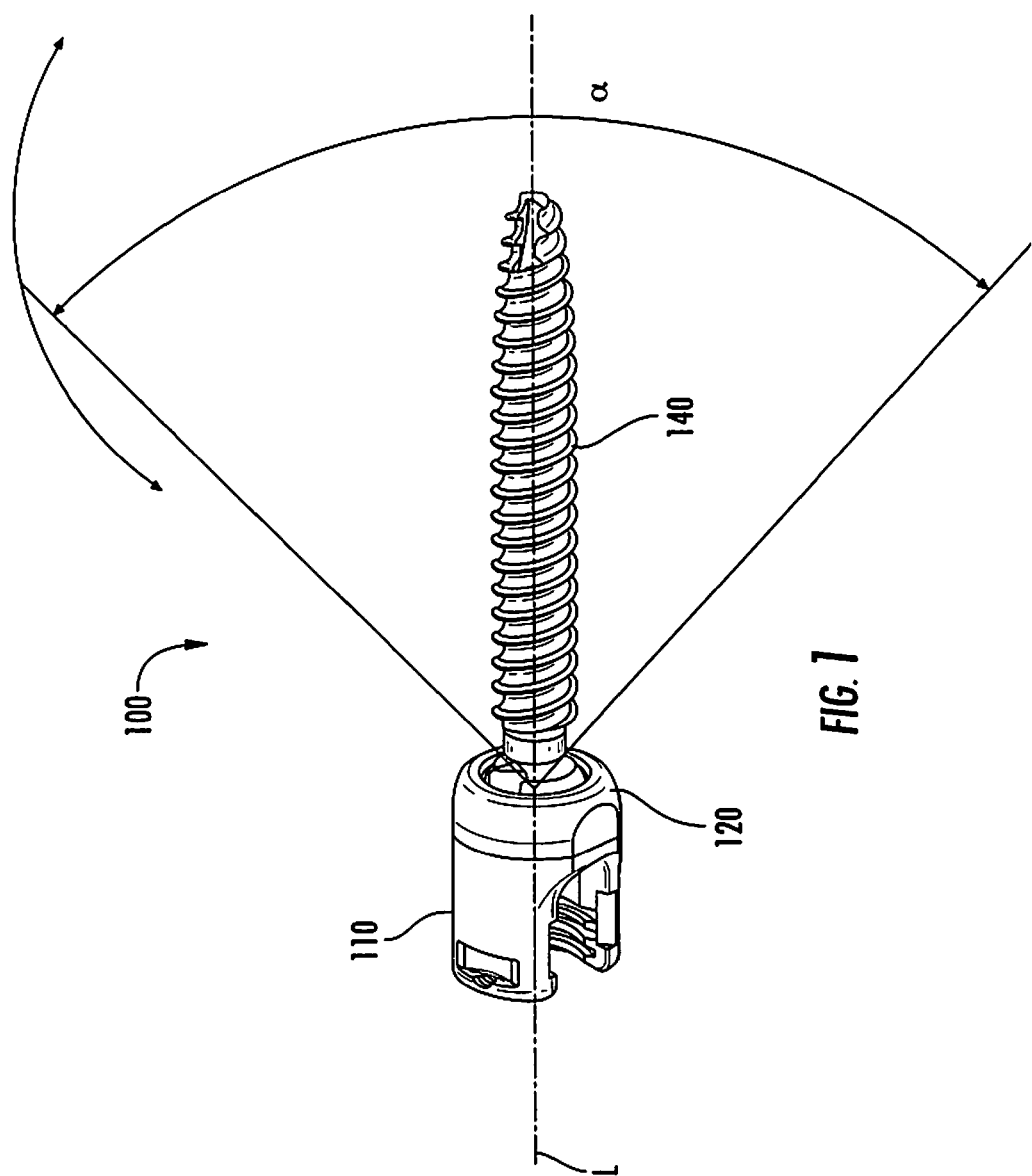
FIG. 1 is a perspective view of one embodiment of a polyaxial pedicle screw in accordance with the present disclosure.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" or "cranial" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (I.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 8:
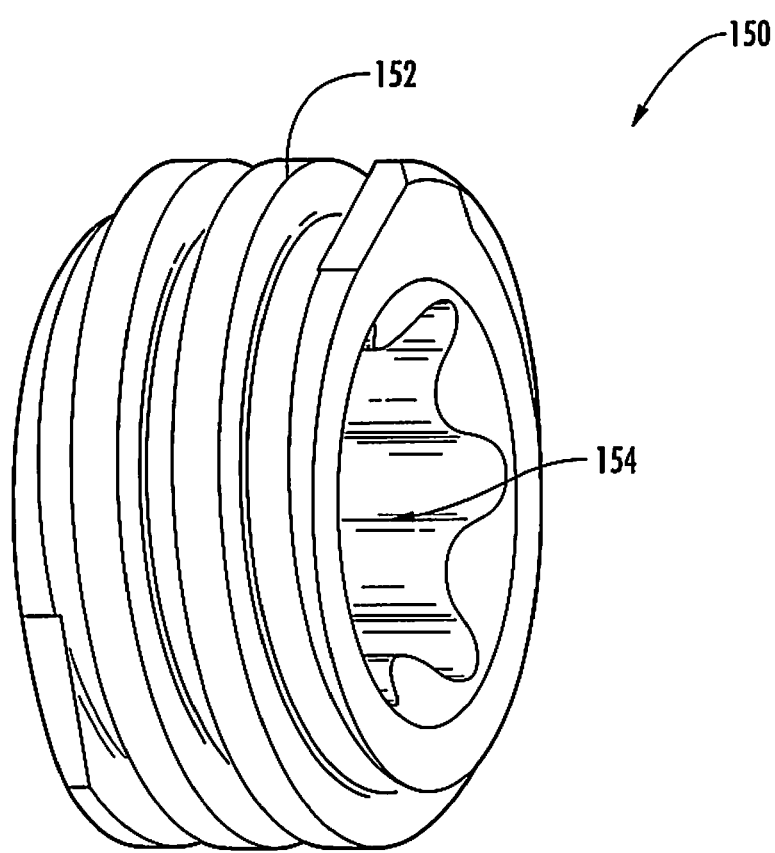
FIG. 8 is a perspective view of a set screw.
Figure 9:
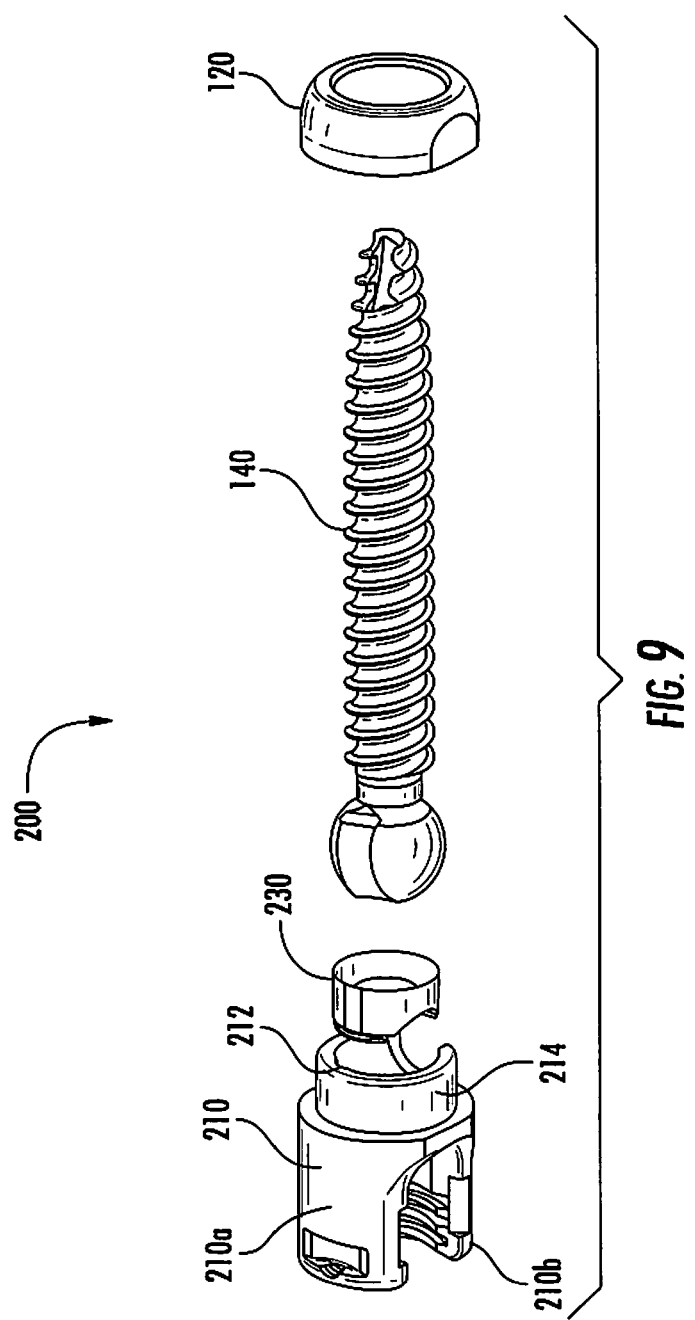
FIG. 9 is an exploded, perspective view of another embodiment of a polyaxial pedicle screw in accordance with the present disclosure.
Figure 10:
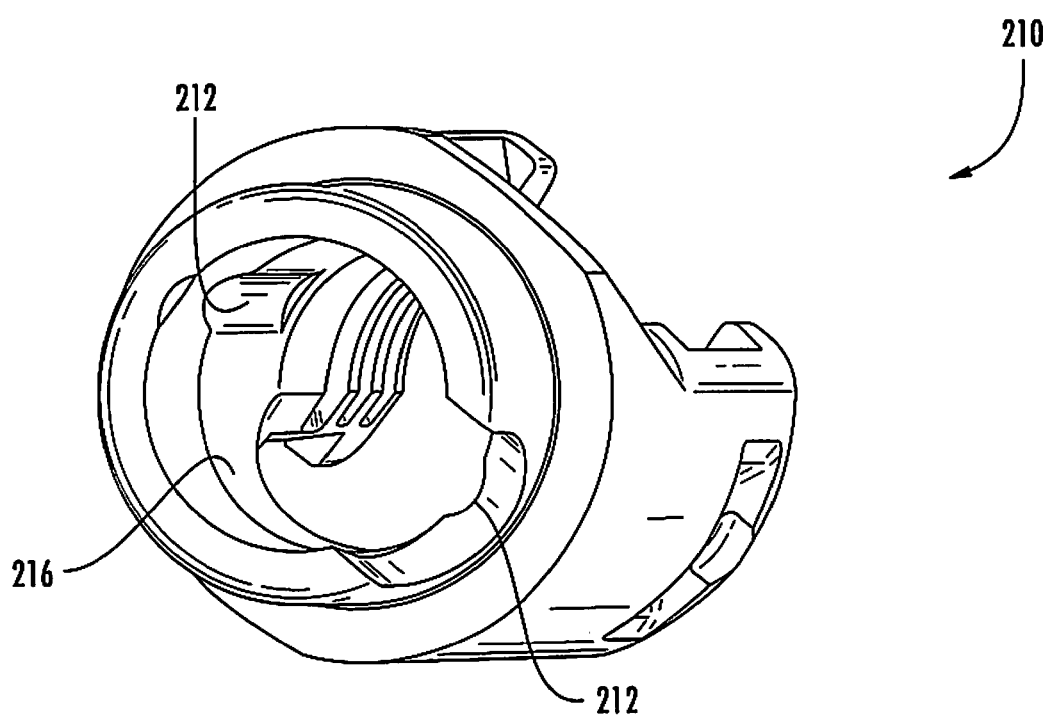
FIG. 10 is a bottom, perspective view of a housing of the polyaxial pedicle screw shown in FIG. 9.
Figure 11:
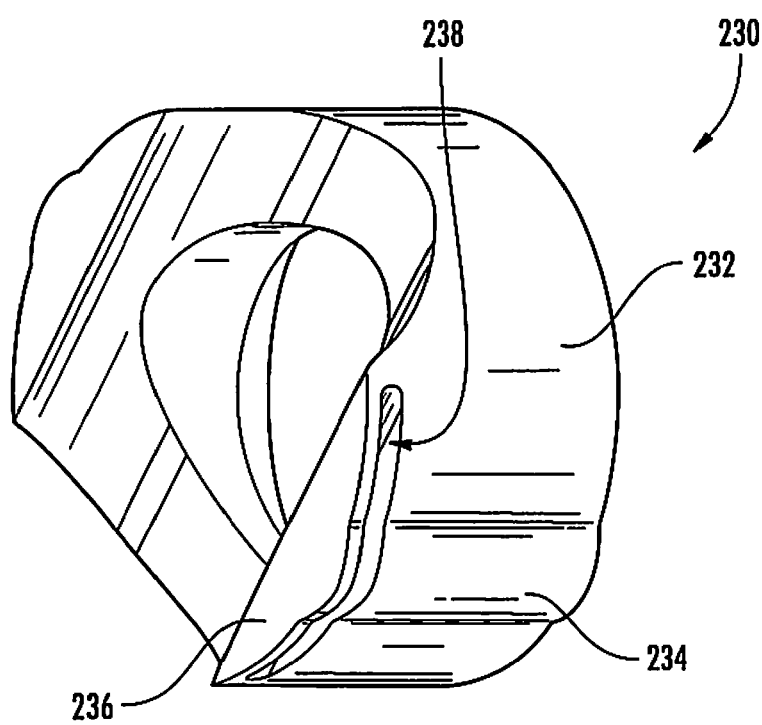
FIG. 11 is a perspective view of an anvil of the polyaxial pedicle screw shown in FIG. 9.

Referring initially to FIGS. 1-4, the present disclosure is directed to a polyaxial pedicle (multi-planar) screw that can provide a connection, via a spinal rod, between adjacent vertebrae not in the same plane. One embodiment of a polyaxial pedicle screw is generally referred to as 100. The polyaxial pedicle screw 100 includes a housing 110, a compression ring or cap 120, an anvil 130, a bone screw member 140, and a set screw 150 (FIG. 8).

Referring to FIGS. 1-5, the housing 110 defines an opening 112 therethrough that permits the reception of any suitable driving instrument (not shown) therethrough. The housing includes opposing walls 110a, 110b that define a V-shaped channel 111 therebetween. Each opposing wall 110a, 110b includes an external flanged recess 113 that is configured to facilitate grasping of the housing 110 by an instrument (not shown) that can also be used to facilitate insertion of the pedicle screw 100 into a pedicle of a vertebral body. The internal surfaces of opposing walls 110a, 110b include threaded portions 115 that are threadably engagable with external threads 152 of the set screw 150 (FIG. 8) to facilitate the securement of a rod member 160 (see FIGS. 12 and 13) within the channel 111 of the housing 110 adjacent the anvil 130.

Figure 2:
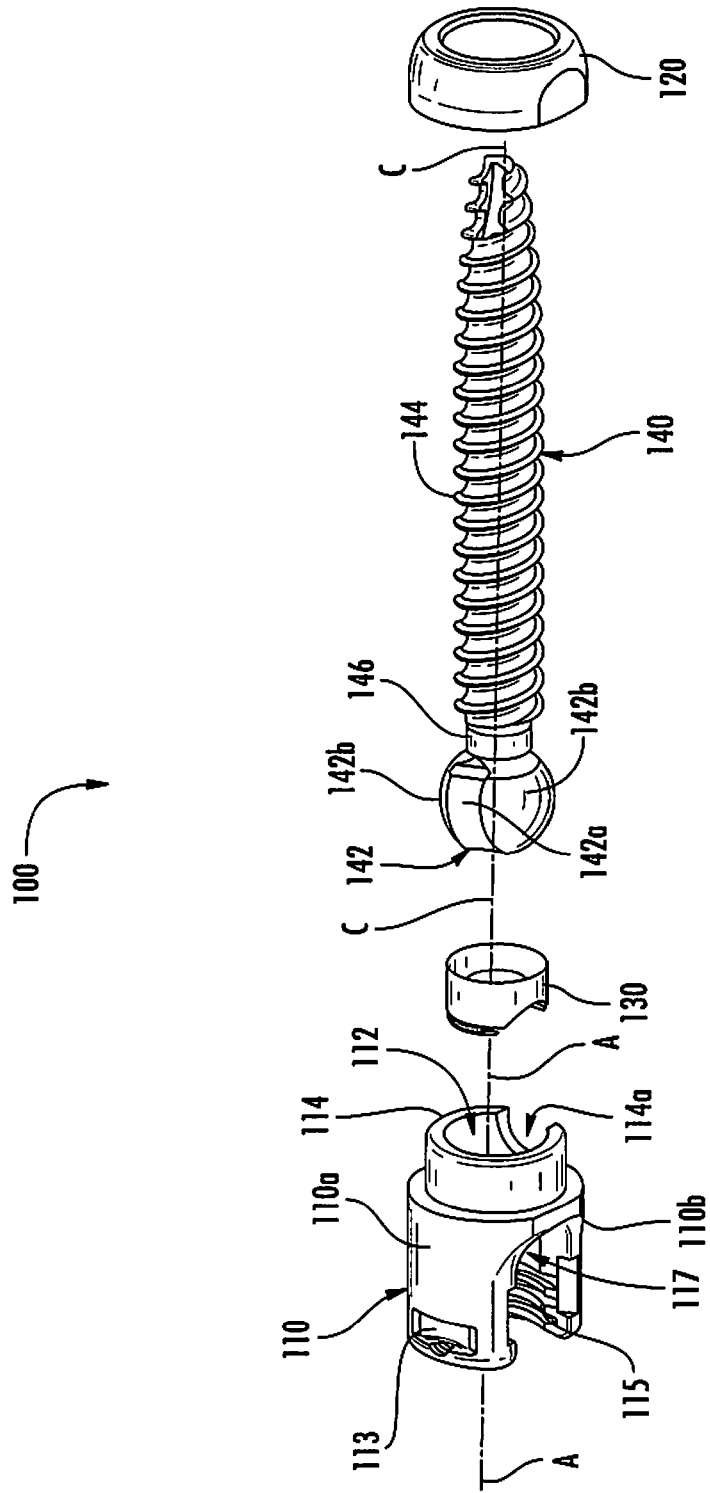
FIG. 2 is an exploded, perspective view of the polyaxial pedicle screw shown in FIG. 1.
Figure 3:
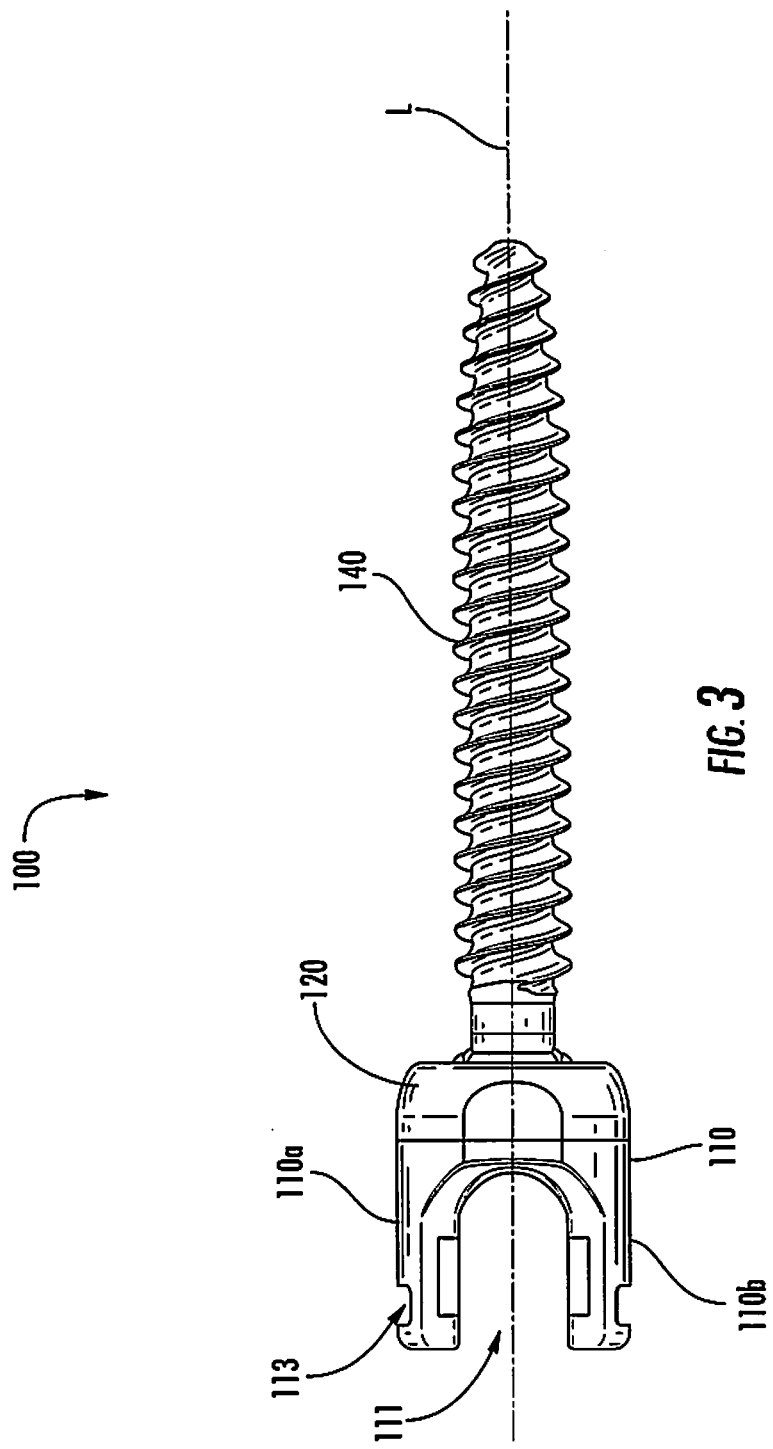
FIG. 3 is a side view of the polyaxial pedicle screw shown in FIG. 1.
Figure 16:
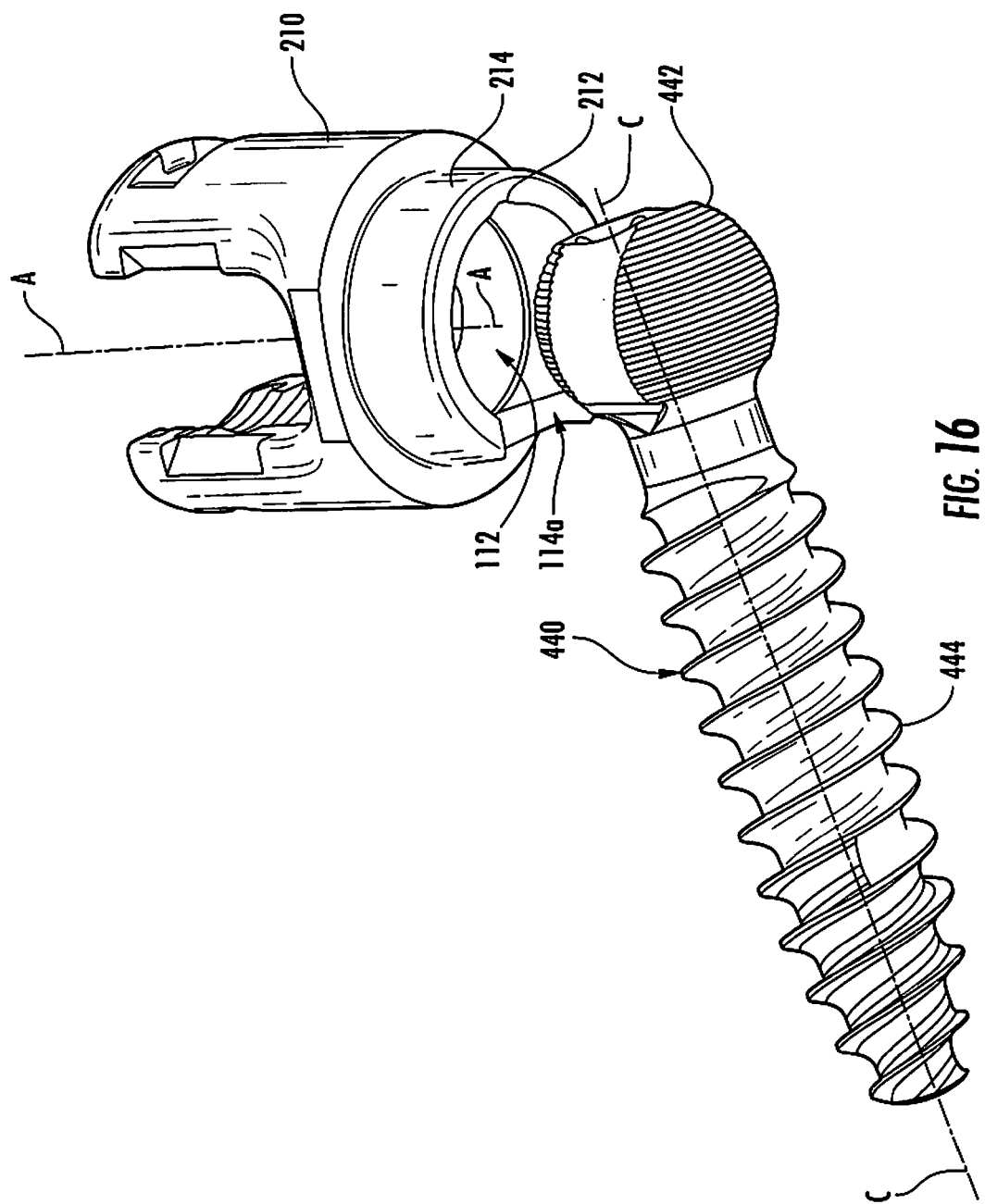
FIGS. 16-17 are progressive perspective views illustrating assembly steps of the polyaxial pedicle screw of FIG. 14 in accordance with the present disclosure.
Figure 17:
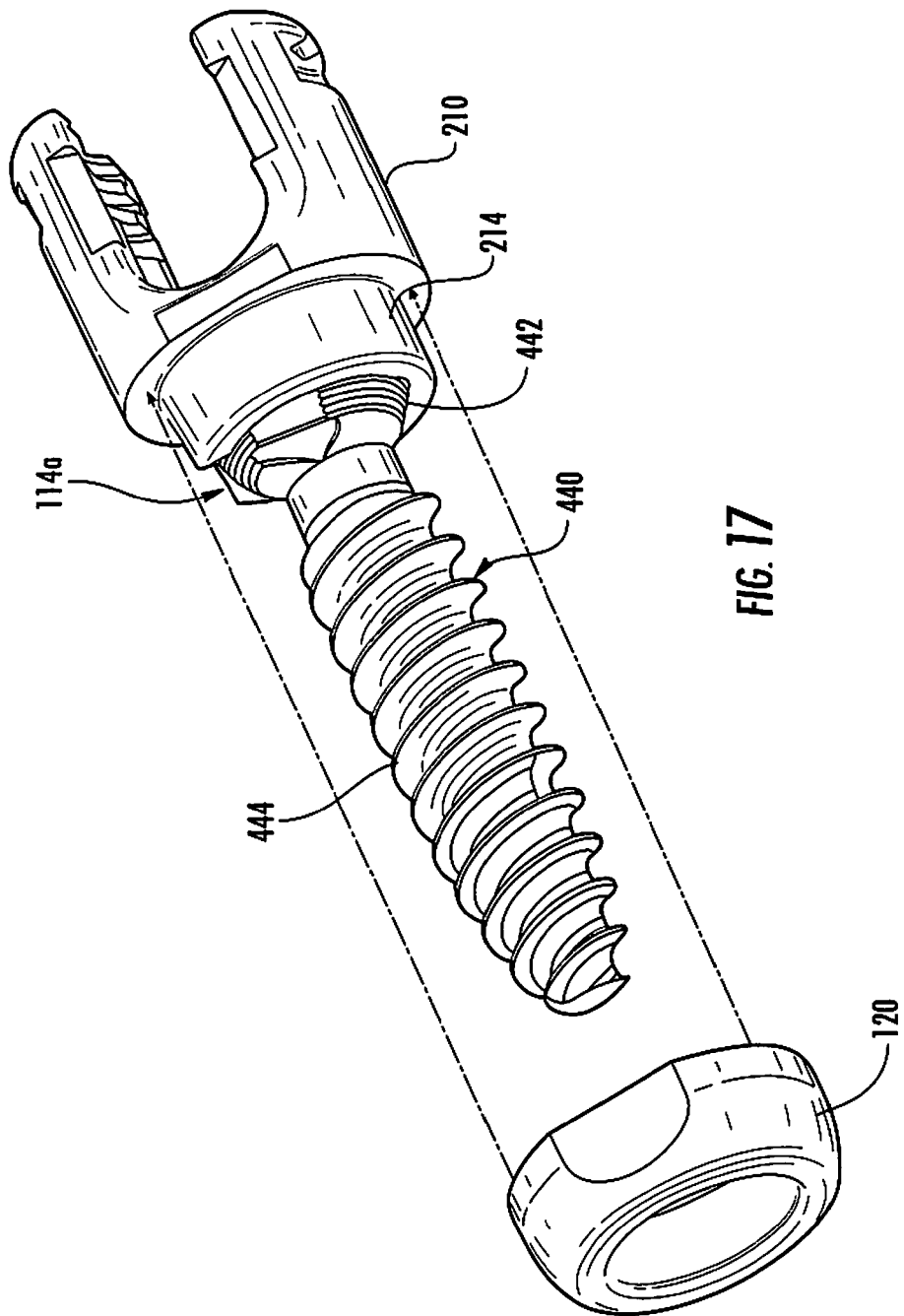
Figure 18:
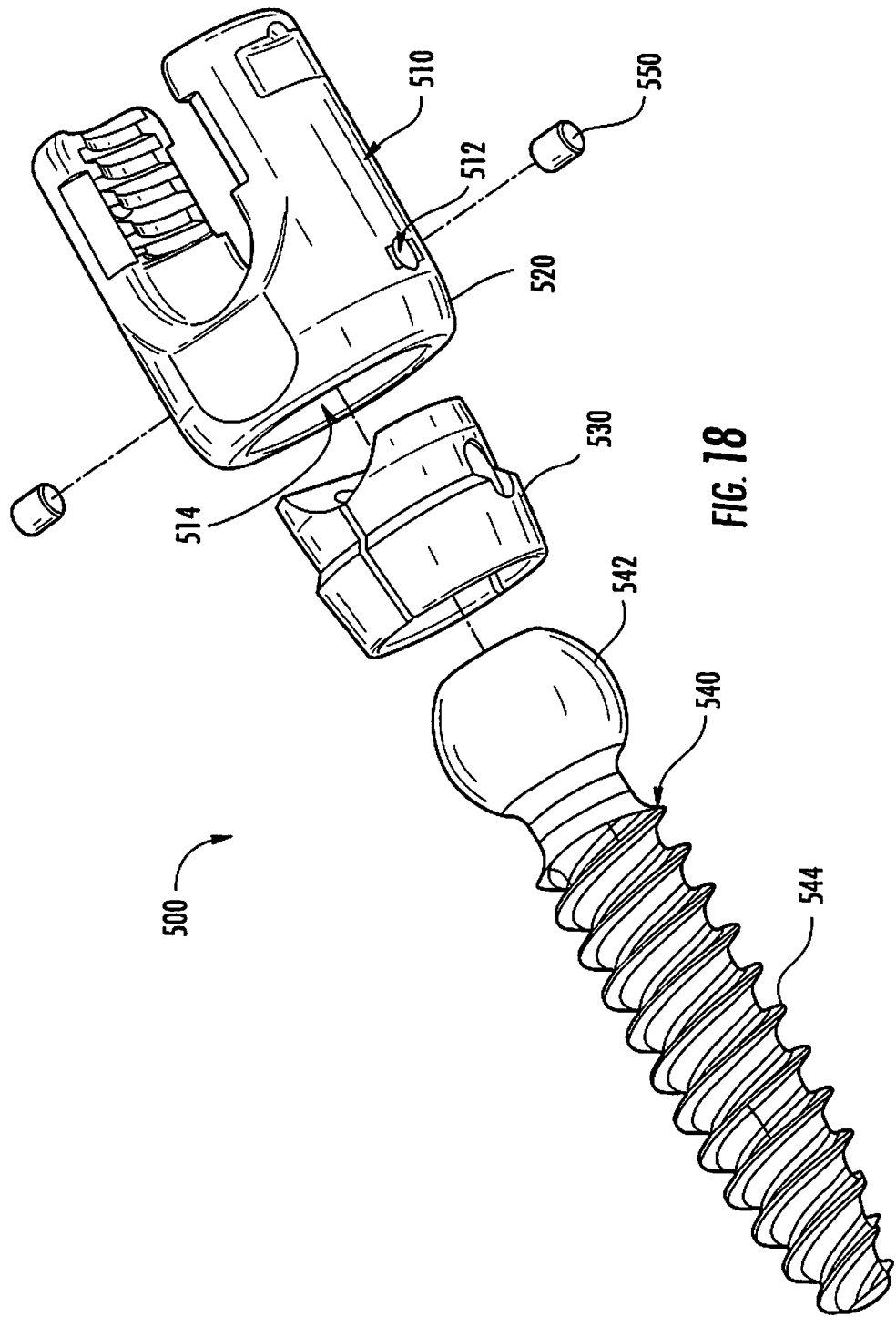
FIG. 18 is an exploded, perspective view of yet another embodiment of a polyaxial pedicle screw in accordance with the present disclosure.

As best shown in FIG. 2, the housing 110 includes a collar 114 extending therefrom. The collar 114 may have a smaller diameter than the diameter defined by the opposing walls 110a, 110b of the housing 110. The collar 114 is adapted to facilitate the securement of the compression ring or cap 120 to the housing 110 once the bone screw member 140 is secured to the housing 110. The collar 114 has a cut out 114a that provides a recess for the reception of a portion of the bone screw member 140, namely a neck 146 of the bone screw member 140. The cut out 114a facilitates the positioning of the bone screw member 140 within the housing 110 from a distal end of the housing 110. In this respect, when the bone screw member 140 is positioned perpendicular (or substantially perpendicular; see e.g., FIG. 16) to the opening 112 (e.g., positioned within a longitudinal axis "L" of the pedicle screw 100 (see FIG. 1) and in axial alignment with a transverse axis "B" extending through cut out 114a (see FIG. 5) such that a longitudinal axis "C" of the bone screw member 140 (see FIG. 2) is perpendicular (or substantially perpendicular) to a longitudinal axis "A" of the housing 110 which extends through opening 112), the neck 146 is positioned within the cut out 114a and a head 142 of the bone screw member 140 is positioned within the opening 112 with cylindrical surfaces (described in greater detail below) of the bone screw head 142 also aligned perpendicular (or substantially perpendicular) to longitudinal axis "A." To this end, upon rotation of a threaded shaft 144 of the bone screw member 140 into coaxial alignment with longitudinal axis "A" of the opening 112 (see e.g., FIG. 17), the head 142, by virtue of a smaller dimensioned cylindrically shaped first portion 142a of the head 142, slides into the housing 110. Once the screw head 142 is disposed inside the housing 110 with the shaft 144 oriented away from the insertion position, a larger dimensioned spherically shaped second portion 142b of the head 142 maintains the bone screw member 140 within the housing 110.

Figure 4:
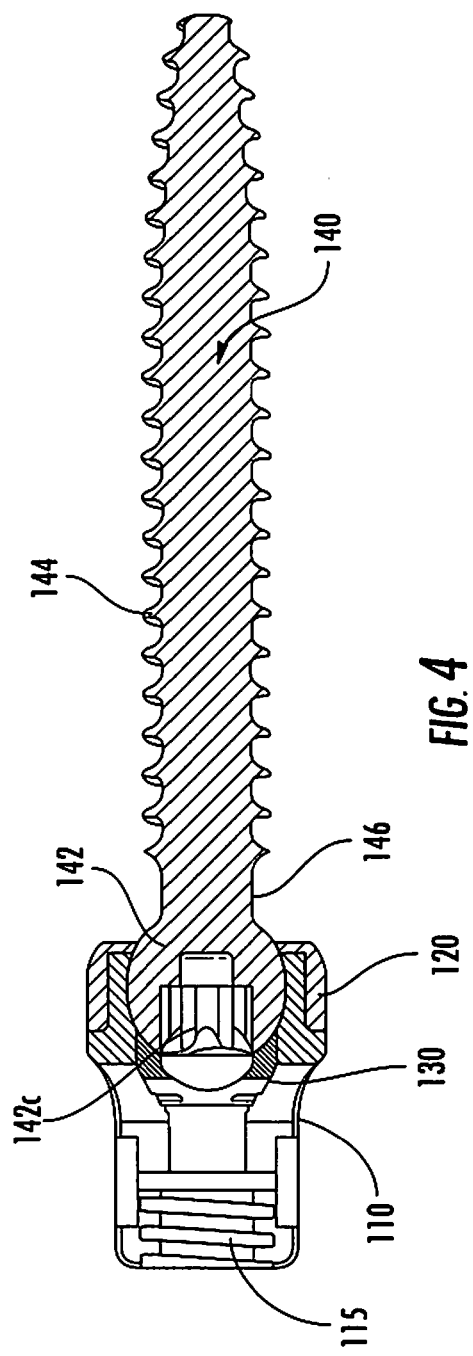
FIG. 4 is a cross-sectional, side view of polyaxial pedicle screw shown in FIG. 1.
Figure 5:
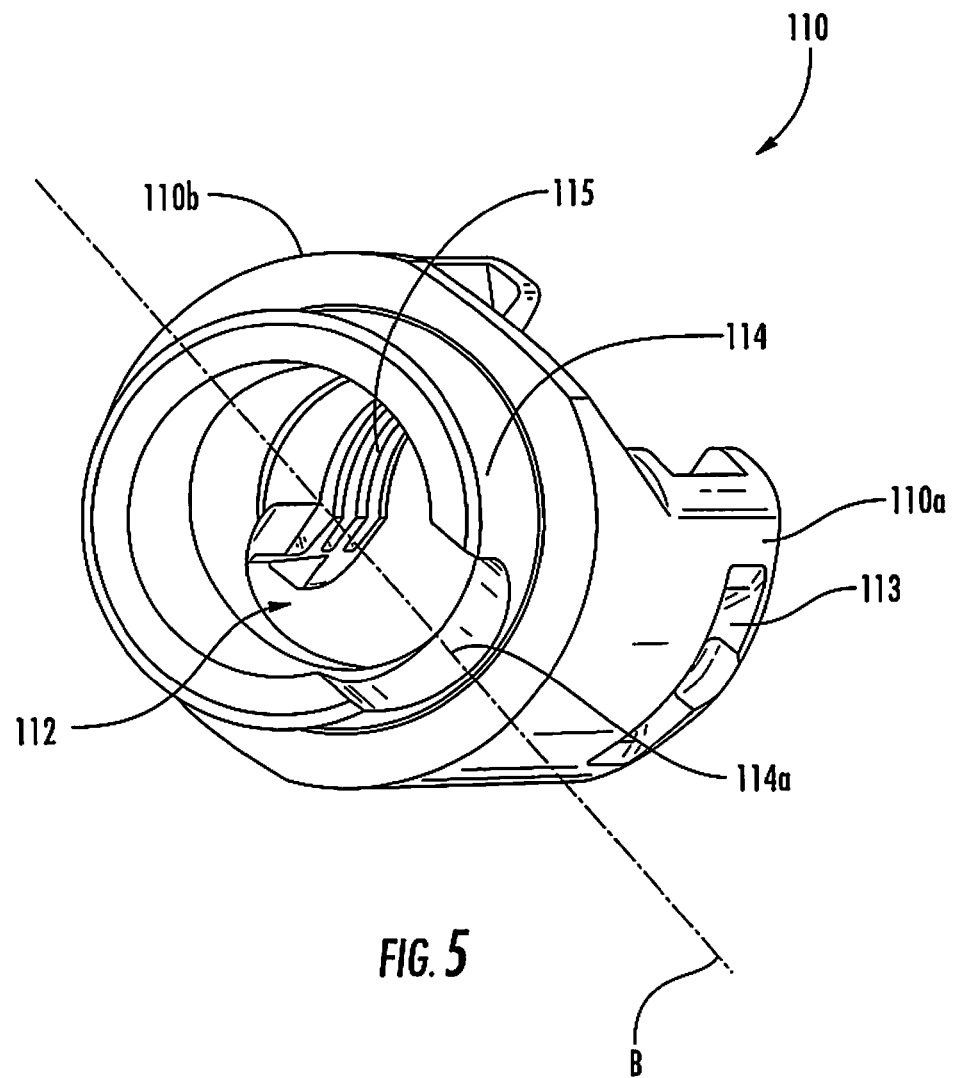
FIG. 5 is a bottom, perspective view of a housing of the polyaxial pedicle screw shown in FIG. 1.

As discussed above, the bone screw member 140 includes a head 142 and a threaded shaft 144 extending from the head 142. The bone screw member 140 may be a self-starting fastener or self-tapping fastener. With reference to FIG. 2, the head 142 is selectively securable within the housing 110 and includes a first portion 142a and a second portion 142b. The head 142, as best illustrated in FIG. 4, includes a driving recess 142c, which may be hexalobular or any other suitable configuration, defined in a proximal surface of the head 142. The driving recess 142c is engagable with any suitable driving instrument (not shown) to enable the driving instrument to advance the bone screw member 140 within bone. The first portion 142a, which may have substantially cylindrical surfaces (but any suitable shape is contemplated), enables the head 142 to fit through the opening 112 defined in the housing 110 from the distal end of the housing 110. In particular, opposed cylindrical surfaces of the first portion 142a may be positioned in co-axial alignment transverse to axis "A" (simultaneously, the opposed spherical surfaces of the second portion 142b are coaxial with axis "A"; see FIG. 16) of the opening 112 (while the shaft 144 is perpendicular to axis "A" by virtue of the neck 146 being seated in cut out 114a) to enable the head 142 to securely fit into housing 110 upon the rotation of the shaft 144 into coaxial alignment with axis "A.". The second portion 142b, which may have substantially spherical surfaces (but any suitable shape is contemplated), maintains the head 142 of the bone screw member 140 within the housing 110 once the head 142 is fully inserted from the distal end of the housing 110 as discussed above.

The effective diameter of the first portion 142a, e.g., the cylindrical section of the screw head 142, is dimensioned to be smaller than the distal opening 112 of the housing 110, so that the cylindrical section can pass through the distal opening 112 into the housing 110. The diameter of the second portion 142b, e.g., the spherical section of the screw head 142, is dimensioned to be larger than the diameter of the distal opening 112 of the housing 110, so that when the screw head 142 is disposed within the housing 110 and the cylindrical section is not aligned with the distal opening 112, the diameter of the spherical section prevents the screw head 142 from exiting the housing 110 through the distal opening 112.

As discussed below, the compression ring or cap 120 may be slid over the shaft 144 and affixed (such as by friction, threading, bayonet mount, gluing, ultrasonic or other welding or the like) to the collar 114 of the housing 110 to further secure the bone screw member 140 to the housing 110. Once inserted, the bone screw member 140 is selectively positionable at plurality of angles relative to the housing 110 when engaged to the housing 110. As illustrated in FIG. 1, the bone screw member 140 may be fixedly securable relative to the housing 110 at a cone angle $\alpha$ in the range of 60 to 80 degrees, preferably 70 degrees, from the longitudinal axis "L" extending through the polyaxial pedicle screw 100.

The compression ring or cap 120 may be securable to the collar 114 to cover the cut out 114a after the head 142 of the bone screw member 140 is positioned within the housing 110 to prevent the bone screw member 140 from re-orienting to a position in which the first portion 142a, namely the cylindrical surfaces, of the head 142 of the bone screw member 140 is aligned with the opening 112 of the housing 110. As can be appreciated, when the bone screw member 140 is positioned within cut out 114a of collar as discussed above, the bone screw member 140 is positioned transverse to the opening 112 and may be oriented with the cylindrical section aligned with the distal housing opening 112 such that the screw head 142 is movable into the housing 110 without inhibition from the second portion 142b, which, as discussed above, otherwise maintains the bone screw member 140 within the housing 110 once the screw head 142 is disposed inside the housing 110. Thus, the compression ring or cap 120 covers the cut out 114a portion of the collar 114 so the shaft 144 of the bone screw member 140 cannot be re-oriented to a position in which the first portion 142a, namely the cylindrical surfaces, of the head 142 are coaxial with the opening 112 of the housing 110.

As depicted in FIG. 4, the anvil 130 is positionable within the housing 110 adjacent the head 142 of the bone screw member 140 when the anvil 130 and the head 142 of the bone screw member 140 are positioned within the housing 110 to facilitate the securement of a rod member 160 (see FIGS. 12-13) within the housing 110. With brief reference to FIG. 8, the set screw 150 is positionable within the housing 110, e.g., via threading engagement, to secure the rod member 160 within the housing 110 adjacent the anvil 130. As can be appreciated, the set screw 150 may be formed of titanium or titanium alloy. The set screw 150 includes a driving interface 154 that is engagable with any suitable driving instrument to threadably engage the set screw 150 within the housing 110.

Figure 6:
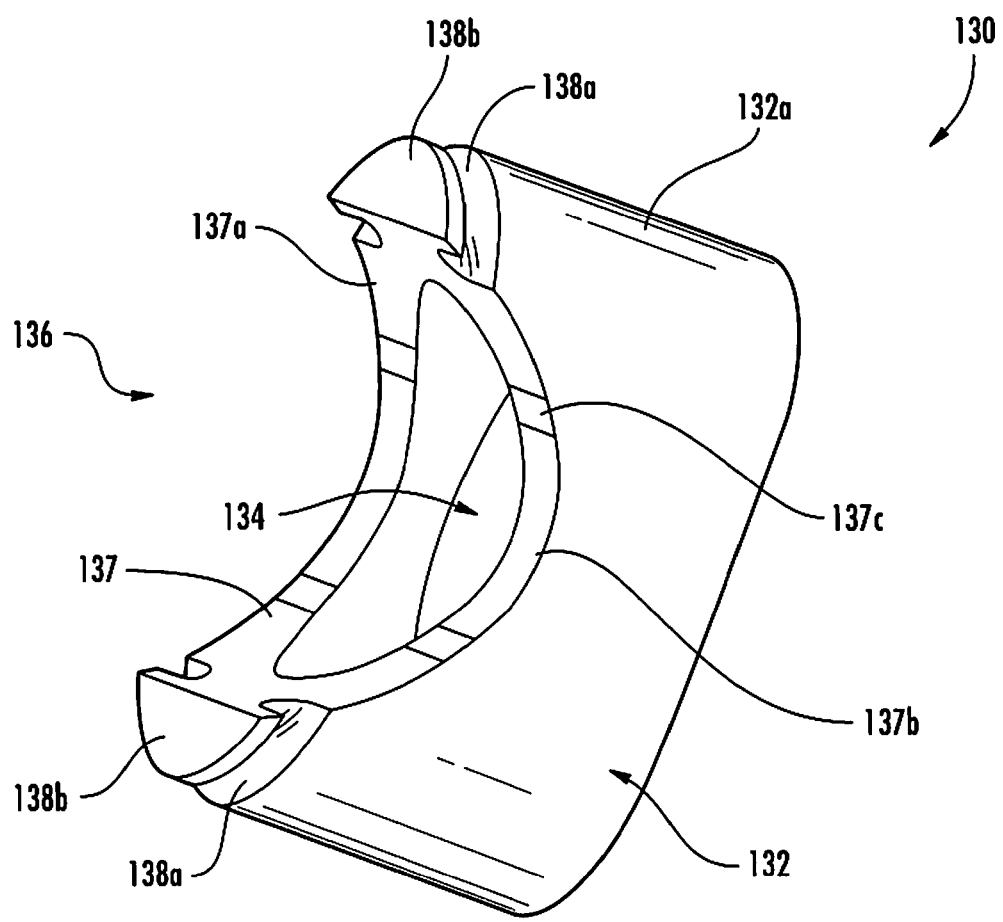
FIG. 6 is a side, perspective view of an anvil of the polyaxial pedicle screw shown in FIG. 1.
Figure 7:
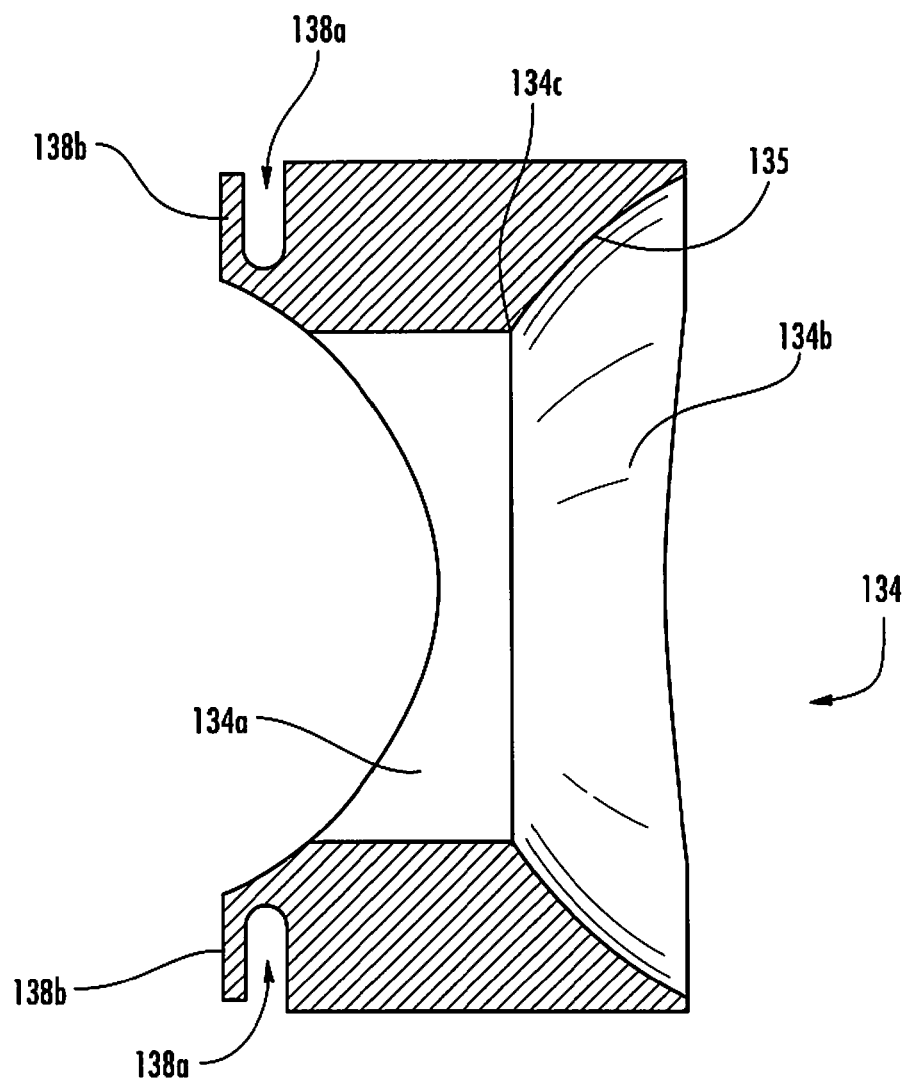
FIG. 7 is a side cross-sectional view of the anvil shown in FIG. 6.

Referring to FIGS. 6-7, the anvil 130 includes a body 132 defining a passage 134 which permits the reception of a driving instrument therethrough. With particular reference to FIG. 7, the passage 134 includes a top portion 134a and a bottom portion 134b separated by an edge 134c. The bottom portion 134b includes arcuate surfaces 135 to accommodate spherical movement of the head 142 of the bone screw 140 when positioned therein. The body 132 also defines an arcuate cavity 136 at a proximal end thereof for the reception of a rod member 160 (FIG. 12) which will be described in greater detail below. The body 132 defines one or more grooves 138a in an outer surface 132a of the anvil 130. Each groove 138a defines one or more flaps 138b. As depicted in FIG. 6, the anvil 130 may include a pair of opposing flaps 138b that act as cantilever beam springs. The one or more flaps 138b are flexibly attached to the anvil 130 adjacent the cavity 136 to enable the anvil 130 to flex an amount sufficient to maintain the head 142 of the bone screw member 140 in constant contact with the anvil 130 when the bone screw member 140 is moved relative to the anvil 130. In this respect, the one or more flaps 138b provide sufficient resistance (against inner surfaces of the housing 20) to prevent any laxity or unintended movement between the anvil 130 and the head 142 of the bone screw member 140. As can be appreciated, the spring force provided by the flaps 138b creates friction between the bone screw member 140 and the housing 110, thus stabilizing the assembly and making it easier to introduce a rod member 160.

Figure 12:
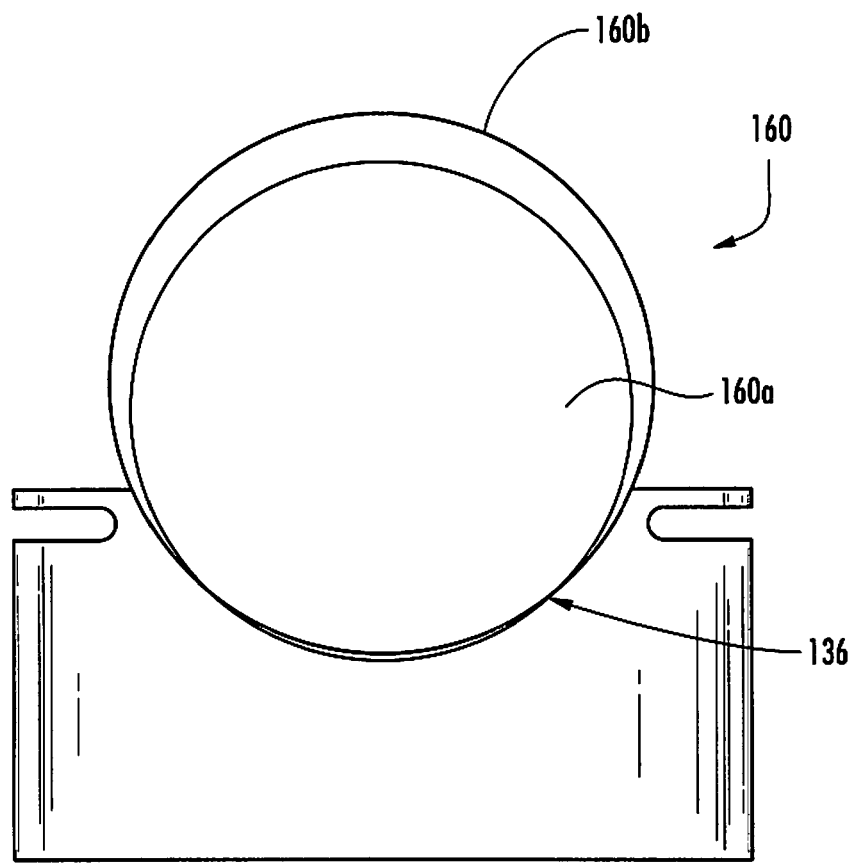
FIG. 12 is a side view of the anvil of FIG. 11 illustrating how variously sized rod members are positioned relative to the anvil.

With continued reference to FIG. 6, the cavity 136 has a surface 137 with a plurality of radii of curvature to accommodate variously sized rod members 160. With brief reference to FIG. 12, a first rod member 160a having a first diameter is shown positioned in the cavity 136; in comparison, a second rod member 160b having a second diameter is also shown positioned in the cavity 136. When first rod member 160a is placed against the arcuate surfaces of the anvil 130, the first rod member 10a nests easily against the anvil 130 because the first rod member 160a closely corresponds to the arc of the arcuate surfaces of the anvil 130. When the second rod member 160b, a larger diameter rod, is positioned against the arcuate surfaces of the anvil 130 and the set screw 150 is tightened against the second rod member 160b, the second rod member 160b is similarly nested in the arcuate surfaces of the anvil 130 but is seated slightly more prominently. Of course, two rod diameters are shown in FIG. 12 for illustrative purposes only, and in practice only one rod at a time could be placed in the housing.

Referring again to FIG. 6, the surface 137 of the cavity 136 defines a first section 137a with a first radius of curvature, a second section 137b with a second radius of curvature, and a third section 137c with a third radius of curvature. In this respect, the plurality of radii of curvature defines a compound curve that provides two or more lines of contact on a plurality of different diameter rod members 160 (e.g., rod members 160a, 160b) without creating a stress riser in the anvil 130 when anyone of a plurality of different diameter rod members 160 is positioned adjacent the compound curve.

The outer surface 132a of the anvil 130 may have a non-round shape, e.g., slightly elliptical, to prevent disorientation of the anvil 130 when positioning the rod member 160 adjacent the anvil 130.

As assembled, the bone screw member is fastenable to a bone structure (e.g. vertebra) and the housing 110 is repositionable in a plurality of directions with respect to the bone screw member 140 as discussed above. To this end, the housing 110 is rotatable about the longitudinal axis "L" (see FIGS. 1 and 3) extending through the polyaxial pedicle screw 100 as well as pivotable relative to the longitudinal axis "L" and the bone screw member 140. A rod member 160, e.g., a spinal rod, is position able in the V-shaped channel 111 of the housing 110 and is nested against the arcuate surfaces of the anvil 130 as discussed above. The rod member 160 is then secured to the polyaxial pedicle screw 100 using a set screw 150 (FIG. 8). To be more specific, the set screw 150 is inserted into a proximal side of opening 112 of the housing 20 adjacent the opposing walls 110a, 110b and rotated such that a distal end of the set screw 150 contacts the surface of the rod member 160 and drives the rod member 160 and the anvil 130 towards the head 142 of the bone screw member 140. Once the desired angular position of the housing 110 is reached, the set screw 150 is tightened further, which compresses the rod member 160, the anvil 130, and the head 142 of the bone screw member 140 within a recess 11 of the housing 110. The frictional engagement between the head 142 of the bone screw member 140 and the bottom portion 134b of the anvil 130 fixes the angular relationship between the housing 110 and the bone screw member 140.

With reference to FIGS. 9-12, one embodiment of polyaxial pedicle screw is generally referred to as 200. Polyaxial pedicle screw 200 is substantially similar to polyaxial pedicle screw 100 and is only described herein to the extent necessary to describe the differences in construction and operation thereof. Polyaxial pedicle screw 200 includes a housing 210, a bone screw member 140, an anvil 230, and a compression ring or cap 120. The housing 210 has one or more slots 212 defined on an inner surface 216 of the housing 210. The slots 212 may extend continuously and/or discontinuously along opposing walls 210a and 210b and/or along a collar 214. The anvil 230 includes one or more flaps 236, one or more grooves 238, and one or more protuberances 234 on an outer surface 232 of the anvil 230. Like flaps 138b, flaps 236 are movable in response to an applied pressure. The protuberances 234 and the slots 212 are engagable to maintain the alignment of the anvil 230 with respect to the housing 210 when the anvil 230 is positioned within the housing 210. One can appreciate that an aligned or substantially aligned arrangement of the anvil 230 with respect to the housing 210 maintains the V-shaped channel 111 in a position to receive a rod member 160 that is aligned with the polyaxial pedicle screw 200. As depicted in FIG. II, the flaps 236 and grooves 238 may be aligned or substantially aligned with the protuberances 234.

Figure 13:
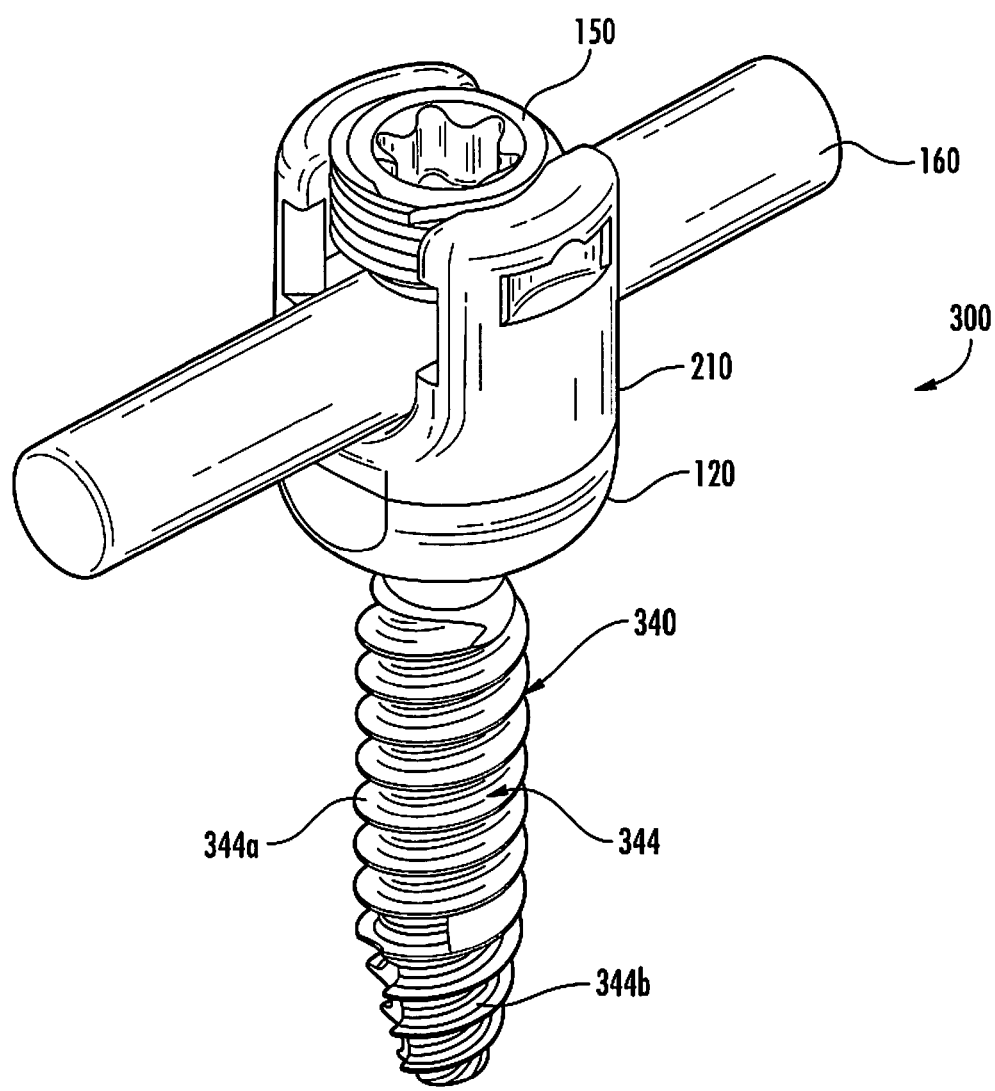
FIG. 13 is a perspective view of another embodiment of a polyaxial pedicle screw with a rod member secured thereto with a set screw in accordance with the present disclosure.

With reference to FIG. 13, one embodiment of a polyaxial pedicle screw, generally referred to as polyaxial pedicle screw 300, is substantial similar to polyaxial pedicle screws 100, 200 and is only described herein to the extent necessary to describe the differences in construction and operation thereof. Polyaxial pedicle screw 300 includes a housing 210, a bone screw member 340, an anvil 230 (see FIG. 11), and a compression ring or cap 120. As illustrated in this embodiment, bone screw member 340 includes a head 142 (see FIG. 2) and a threaded shaft 344. The threaded shaft 344 includes a first threaded segment 344a and a second threaded segment 344b.

Figure 14:
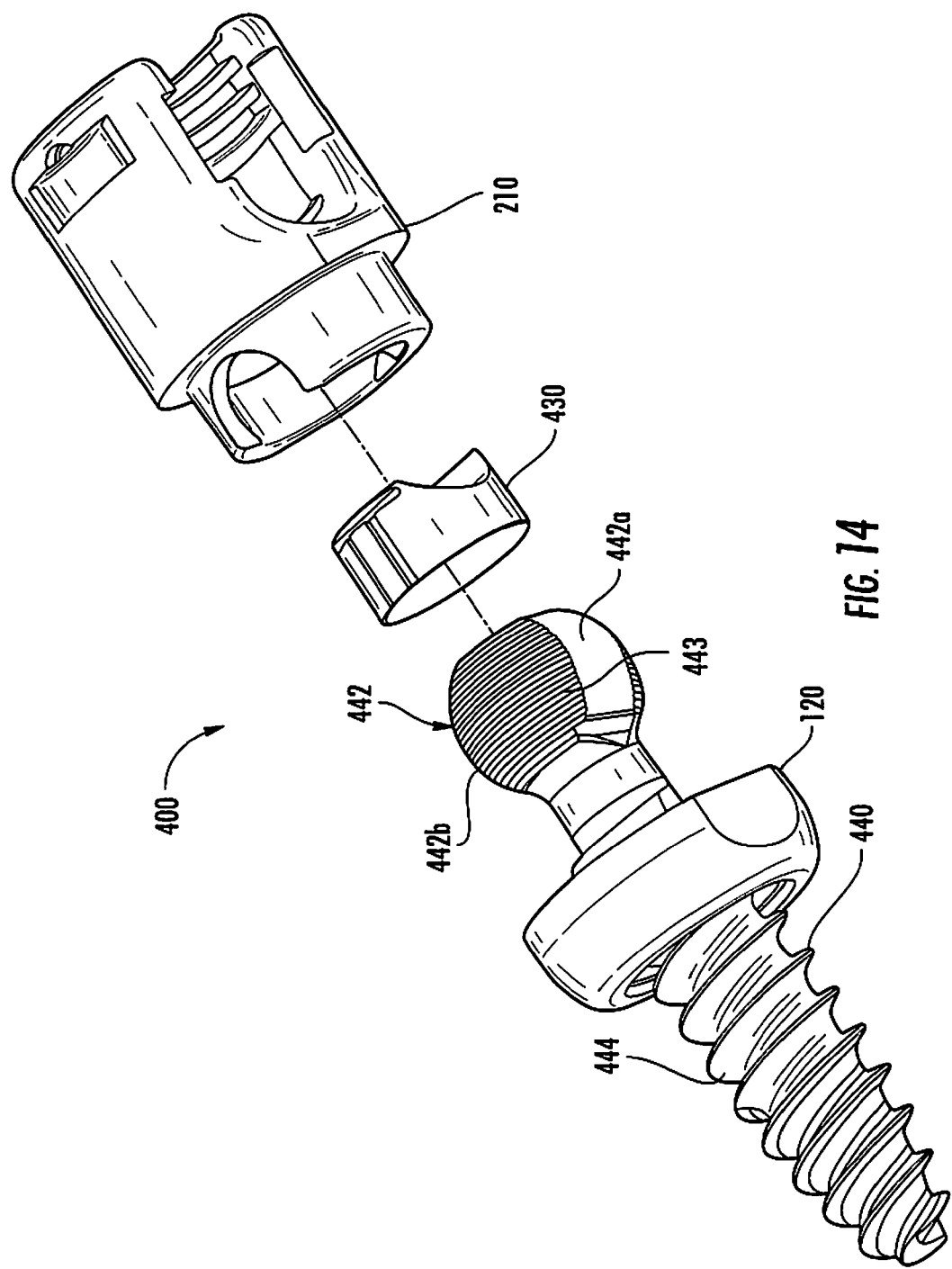
FIG. 14 is an exploded, perspective view of yet another embodiment of a polyaxial pedicle screw in accordance with the present disclosure.
Figure 15:
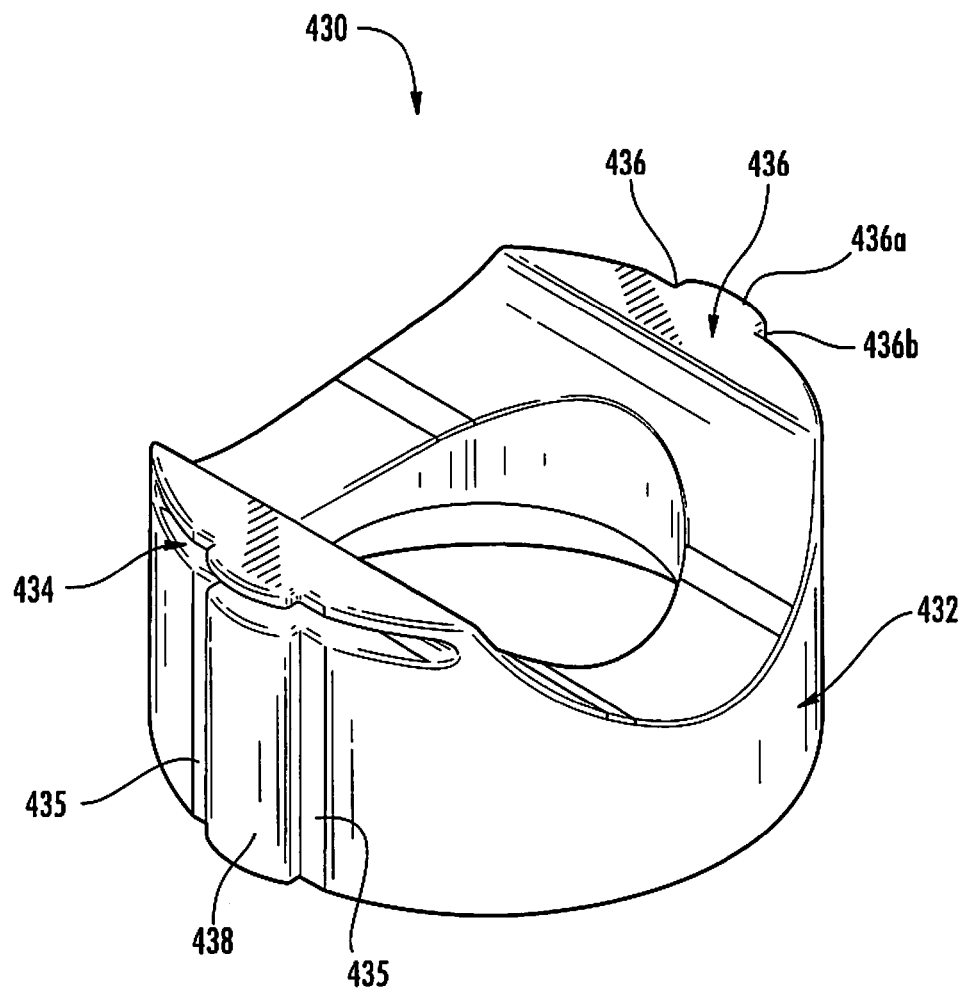
FIG. 15 is an enlarged, perspective view of an anvil of the polyaxial pedicle screw shown in FIG. 14.

With reference to FIGS. 14 and 15, one embodiment of a polyaxial pedicle screw, generally referred to as polyaxial pedicle screw 400, is substantial similar to polyaxial pedicle screws 100,200,300 and is only described herein to the extent necessary to describe the differences in construction and operation thereof. Polyaxial pedicle screw 400 includes a housing 210, a bone screw member 440, an anvil 430, and a compression ring or cap 120. Bone screw member 440 includes a head 442 and a threaded shaft 444. The head 442 includes a first portion 442a and a second portion 442b. The second portion 442b includes surface texture 443, e.g., serrations, to facilitate the frictional engagement with the anvil 430 and/or the housing 210 such that a user is required to apply some minimal force to move the bone screw member 440 relative to the anvil 430 and/or the housing 210. In this respect, the bone screw member 440 frictionally engages with the anvil 430 such that a user applied force (e.g., beyond gravity forces) is necessary to reposition the bone screw member 440 relative to the anvil 430 when the bone screw member 440 is disposed in engagement with the anvil 430.

As best depicted in FIG. 15, the anvil 430 includes a body 432. The body 432 includes a pair of opposing grooves 434, a pair of opposing flaps 436, and a pair of opposing protuberances 438. The body 432 also defines a pair of notches 435 that extend along each protuberance 438. The opposing flaps 436 each include a protuberance 436a positioned between a pair of notches 436b. The protuberance 436a and pair of notches 436b may be aligned or substantially aligned with protuberances 438 and pair of notches 435, respectively, as illustrated in FIG. 15.

With reference to FIGS. 18-21, one embodiment of polyaxial pedicle screw is generally referred to as 500. Polyaxial pedicle screw 500 is substantially similar to polyaxial pedicle screws 100, 200, 300, 400 and is only described herein to the extent necessary to describe the differences in construction and operation thereof. Polyaxial pedicle screw 500 includes a housing 510, a compression ring or cap 520, an anvil 530, a bone screw member 540, and one or more pins 550. The housing 510 is positionable on a head 542 of the bone screw member 540. The housing 510 defines one or more pin channels 512 therethrough for the reception of a pin 550 to secure at least a portion of the anvil 530 within the housing 510.

Figure 19:
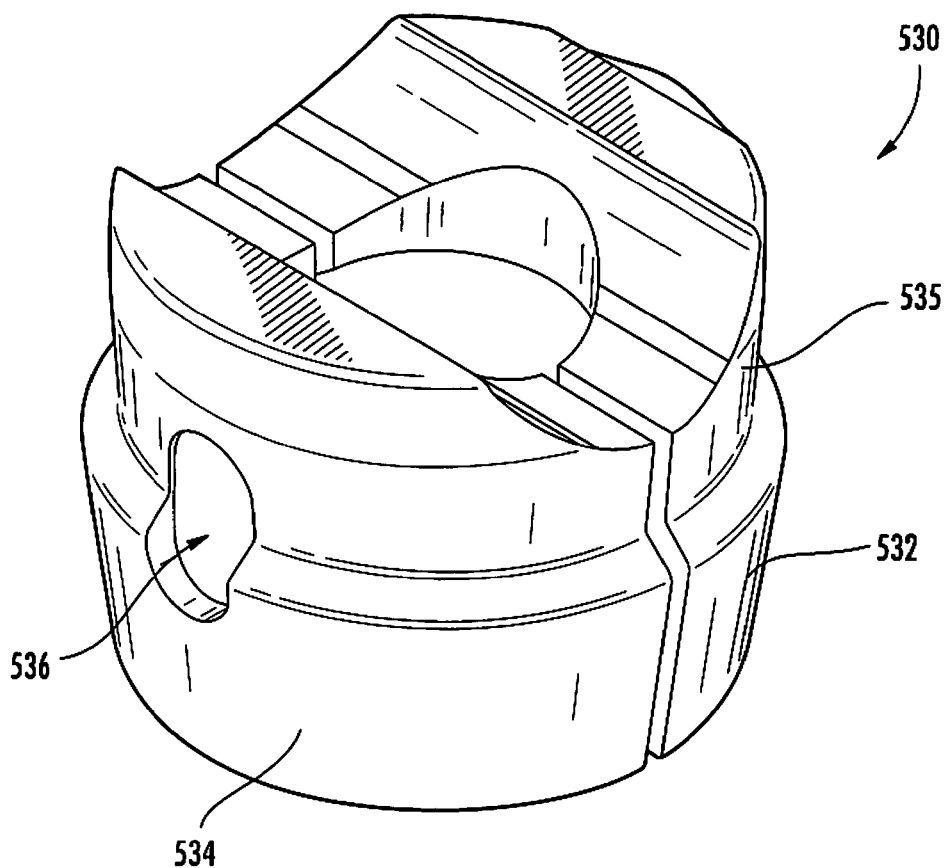
FIG. 19 is a perspective view of first and second wedge members of the polyaxial pedicle screw shown in FIG. 18.
Figure 20:
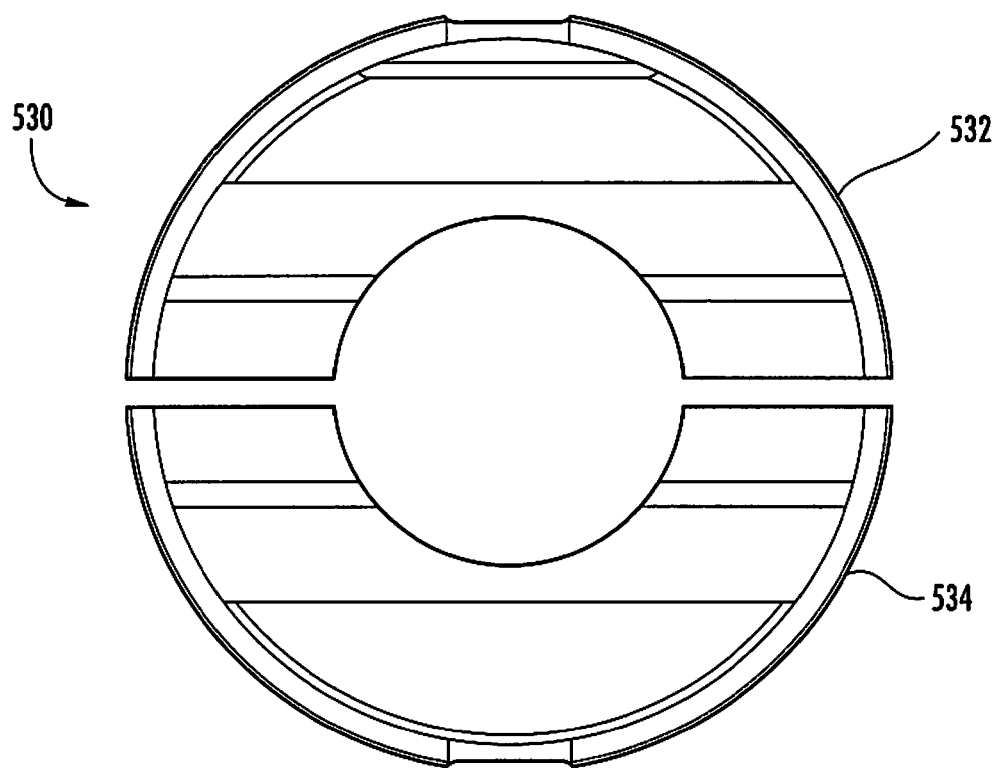
FIG. 20 is top view of the first and second wedge members shown in FIG. 19.
Figure 21:
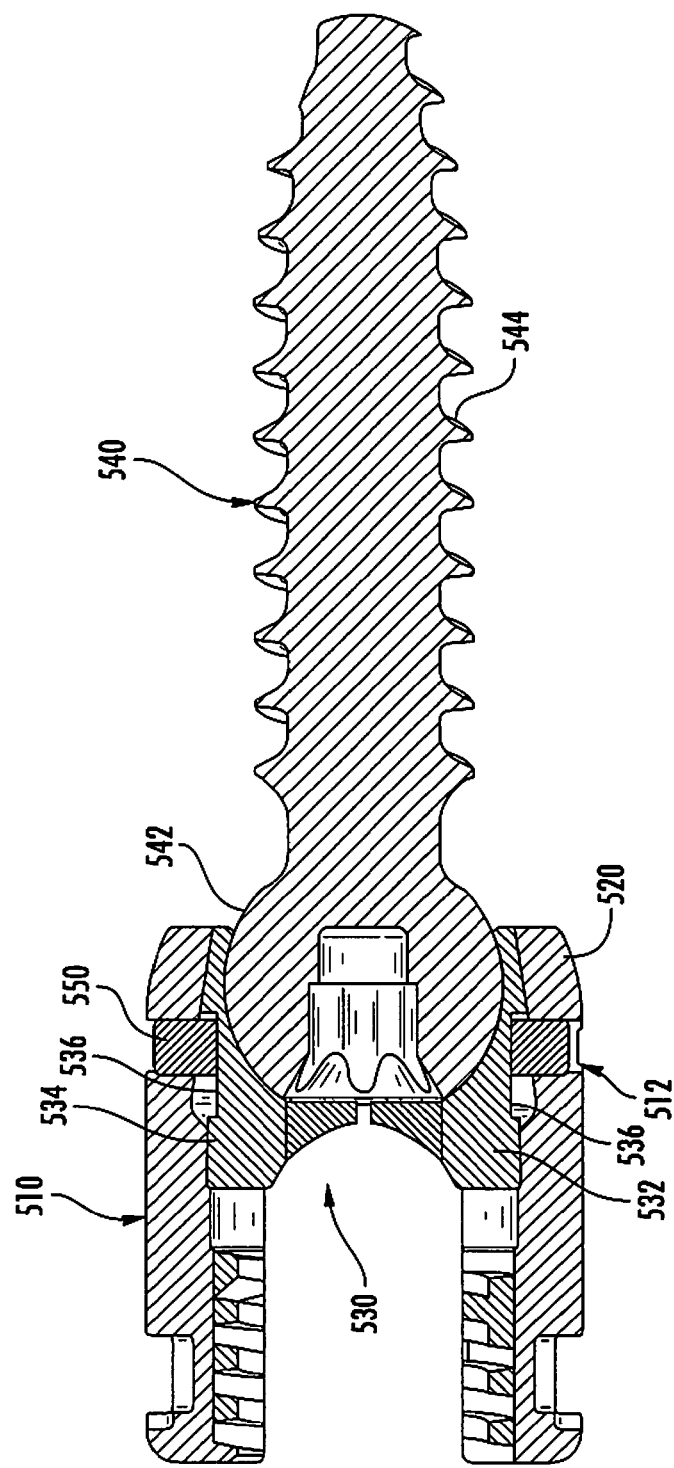
FIG. 21 is a cross-sectional view of the polyaxial pedicle screw in an assembled configuration.

As shown in FIGS. 19-21, the anvil 530 includes a first wedge member 532 and a second wedge member 534. The first and second wedge members 532, 534 are separate and distinct sections of the anvil 530, as most clearly illustrated in FIG. 20. Each wedge member 532, 534 is positionable within the housing 510 adjacent the head 542 to facilitate the securement of the head 542 of the bone screw member 540 and a rod member 160 (see FIG. 13) within the housing 510. Each wedge member 532, 534 defines one or more pin pockets 536 in an outer surface 535 thereof. In this respect, a pin 550 is positionable within the one of the pin channels 512 and one of the pin pockets 536 to maintain one of the first and second wedge members 532, 534 within the housing 510, as best illustrated in FIG. 21. As can be appreciated, any number of wedge members, pins, and/or pin channels may be utilized. In this embodiment, the head 542 of the bone screw member 540 need not be configured to have both cylindrical and spherical shaped sections, and the entire head 542 can be substantially spherical. During assembly, each wedge 532, 534 is disposed within the housing 510 in its proximal-most position, such that the spherical head 542 may enter a bottom opening 5140*f* the housing 510 unimpeded. Once the head 542 is inserted, the wedges 532, 534 drop from their proximal position to embrace the head 542 and prevent the head 542 from being withdrawn from the housing 510.

A kit of the presently disclosed polyaxial pedicle screws may include two or more polyaxial pedicle screws of the present disclosure and one or more rod members 160.

As can be appreciated, any portion of any of the presently disclosed polyaxial pedicle screws can be formed of formed of titanium, titanium alloy, stainless steel, cobalt chrome, or other metal or polymeric materials. In this regard, it is also appreciated that utilizing a combination of compatible materials in the screw assembly may be advantageous. Thus, it is contemplated that the housing could be made of a harder or stiffer material such as cobalt chrome, while the screw and anvil and set screw may be made of another, compatible material such as titanium or titanium alloy. Further, components of any of the presently disclosed embodiments may be press fit, staked, pinned, or welded together.

Any embodiments of the bone screw members presently disclosed pedicle screws may have a single lead thread or a double lead thread (e.g., two starts) to facilitate insertion into and fixation within bone. In particular, in a double lead thread configuration, a pair of helical threads may be offset by 180 degrees so that the lead of threads is approximately equal to double the pitch of the threads. In other words, the axial distance that bone screw members with a double lead thread configuration travel during one full 360 degree rotation is approximately double the distance between adjacent crests of the threads. The lead may be in the range of about 1 mm to about 3 mm, preferably about 2 mm, while the pitch of each of the threads may be in the range of about 2 mm to about 6 mm, preferably about 4 mm. Thus, while the adjacent crests are only about 2 mm apart from one another, the bone screw member with a double lead thread configuration travels a distance of about 4 mm per revolution. Further, as shown in FIG. 13. A distal segment of the shaft of a bone screw member may taper distally to a distal tip of the shaft. Specifically, both the inner and outer diameters of the shaft of the bone screw member may taper distally, e.g., the shaft and the threads may taper distally.

Figure 23:
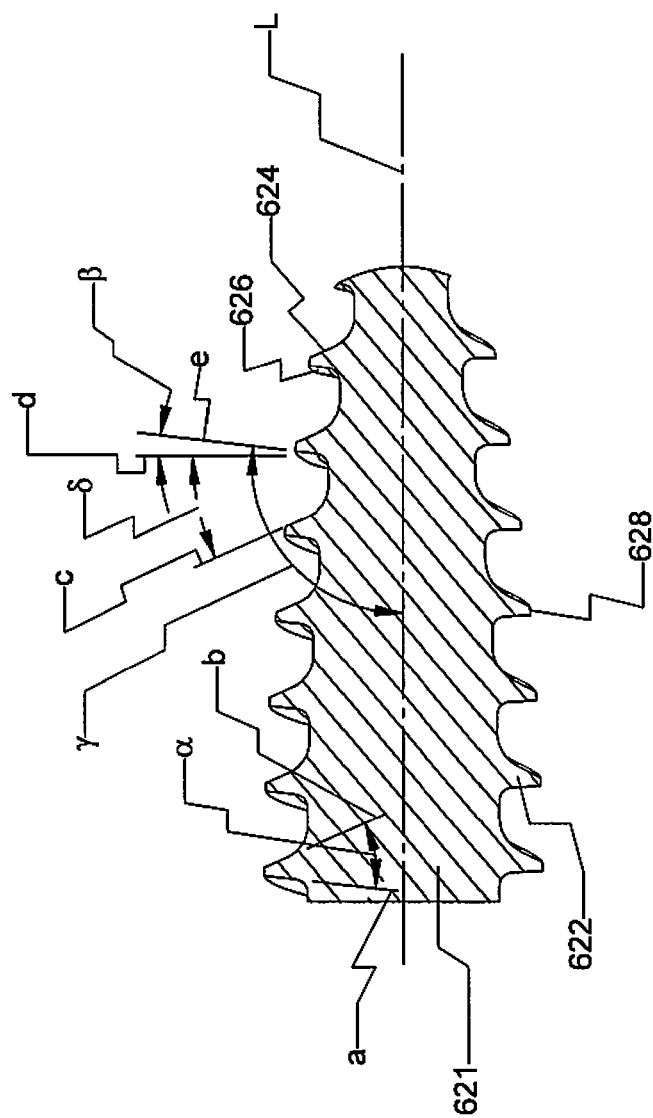
FIG. 23 is an enlarged cross-sectional view of the indicated area of detail shown in FIG. 2.

Additionally, any embodiments of the bone screw members of the presently disclosed pedicle screws may be provided in any suitable diameter size and/or length. Some of the bone screw members may have diameters of approximately 4.5, 5.5, 6.5, 7.5, 8.5, 9.5, and 10.5 mm and may have lengths of approximately 25-115 mm. For example, the thread dimensions on a 6.5 mm diameter bone screw member may include a major diameter of about 0.256 inches and a minor diameter of about 0.177 inches through the proximal or trailing two-thirds (⅔) of the screw length. As shown in FIGS. 13 and 23, the distal or leading third (⅓) of the length of the shaft, which is the distal portion of the bone screw member, may taper, for example, to about a 0.150 inches major diameter at the distal tip of the distal third of the length of the shaft. This taper may follow a radius of about 3.582 inches for a 6.5 mm diameter and 45 mm length screw. This radius is defined by the tip diameter as well as its tangency with the major diameter at the start of the taper. Therefore, the radius varies by diameter and length of the bone screw member.

Figure 22:
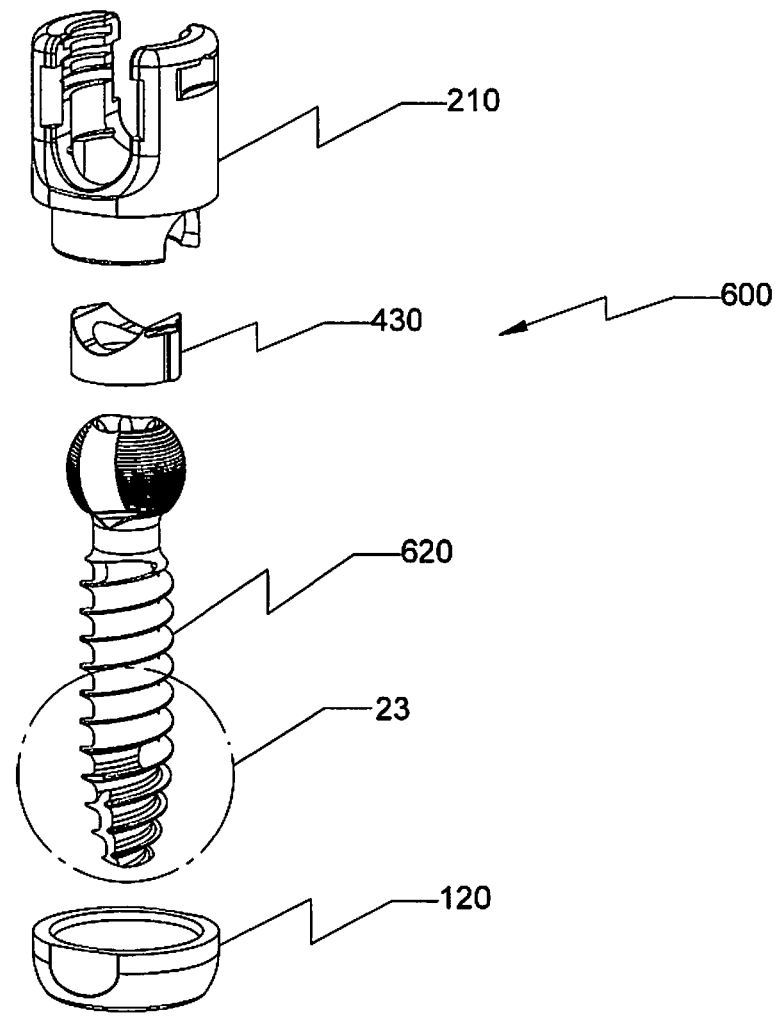
FIG. 22 is an exploded perspective view of another embodiment of a polyaxial pedicle screw in accordance with the present disclosure.
Figure 24:
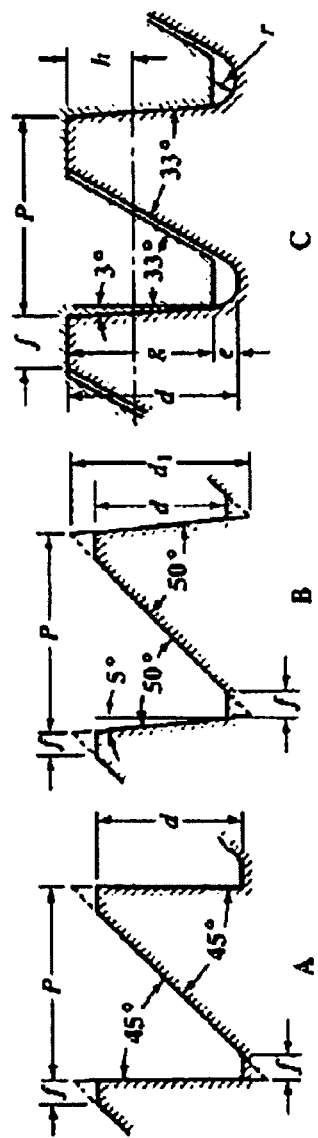
FIG. 24 illustrates various thread forms of embodiments of the presently disclosed polyaxial pedicle screw.

Referring also to FIG. 22, any embodiments of the bone screw members of the presently disclosed pedicle screws may have a buttress thread form arrangement that has improved pullout strength as compared to competitive products (see Tables 1 and 2, below). Various thread form arrangements of embodiments of the presently disclosed pedicle screws are illustrated in FIG. 24.

With reference to FIGS. 22-23, one embodiment of polyaxial pedicle screw is generally referred to as 600. Polyaxial pedicle screw 600 is substantially similar to polyaxial pedicle screw 100 and is only described herein to the extent necessary to describe the differences in construction and operation thereof. Polyaxial pedicle screw 600 includes a housing 210, a bone screw member 620, an anvil 430, and a compression ring or cap 120.

As shown in FIG. 23, bone screw member 620 of pedicle screw 600 includes a buttress thread form that is arranged so that a pressure flank 622 of the buttress thread form is disposed at an angle gamma "γ" relative to the thread or shaft axis "L" extending between leading and trailing ends of shaft 621 (e.g., the angle defined between shaft axis "L" and line "e") of bone screw member 620. Angle gamma "γ" may be nearly perpendicular, for example, approximately 95 degrees, so that the radial component of the thrust taken by the pressure flank 622 during pullout is reduced to a minimum to increase the pullout strength of the screw. More particularly, the thread may have a leading edge 624 that extends at an angle delta "δ" relative to vertical (i.e., line "d" which is an orientation that is perpendicular to a shaft axis "L"). Angle delta "δ", which extends between lines "c" and "d", may be about 45 degrees. A trailing edge 626 of the thread is disposed at an angle beta "β" relative to vertical. Angle beta "β", which extends between line "d" (vertical) and line "e", may be about −5 degrees. In this regard, as delineated with lines "a" and "b", the leading and trailing ends 624, 626 define an angle alpha "a" therebetween that is equal to angle delta "δ" plus angle beta "β." The width of the crest 628 may be about 0.007 inches.

As provided in Tables 1 and 2 below, the pullout strength of various pedicle screws were tested in a 10 lb/ft$^3$ foam and a 20 lb/ft$^3$ foam. Notably, the data provided in Tables 1 and 2 indicate statistically significant differences among the pedicle screws. The pedicle screws tested included pedicle screw 600, a taper lock screw as shown and disclosed in application Ser. No. 12/739,461 filed on Apr. 23, 2010, which is incorporated herein by reference, a set screw as shown and disclosed in application Ser. No. 12/739,506, filed on Apr. 23, 2010, which is incorporated herein by reference, and competitor screws 1-9.

TABLE 1

Variation in overall pullout strength of all tested screws in 10 lb/ft³ foam.
(n = 30 for all pedicle screws)
(all pedicle screws inserted in 20 mm depth)

| Pedicle Screw | OD | Mean (N) | SD (N) |
|---|---|---|---|
| Pedicle Screw 600 | 6.5 | 343.80 | 21.21 |
| Competitor 1 | 6.5 | 313.59 | 17.38 |
| Taper Lock Screw | 6.5 | 306.61 | 21.37 |
| Competitor 2 | 7.0 | 296.97 | 19.23 |
| Competitor 3 | 6.0 | 291.84 | 12.72 |
| Set Screw | 6.5 | 291.50 | 16.94 |
| Competitor 4 | 6.5 | 290.68 | 9.87 |
| Competitor 5 | 6.5 | 265.67 | 20.58 |
| Competitor 6 | 6.5 | 253.96 | 22.47 |
| Competitor 7 | 5.5 | 203.45 | 9.91 |
| Competitor 8 | 5.0 | 177.78 | 5.93 |
| Competitor 9 | 5.5 | 163.71 | 11.28 |

For comparison purposes, testing results collected from the 20 lb/ft³ are displayed in Table 2 below. Note that the mean peak load values are substantially higher than those found in Table 1. Values typically range from 900-1200N, again well within the values of the standard. Note that the ranking of the screws has changed due to the fact that the test was run using (simulated) denser bone which is more indicative of the bone in the pedicle of a healthy patient.

TABLE 2

Variation in overall pullout strength of all tested screws in 20 lb/ft³ foam.
(n = 30 for all pedicle screws)
(all pedicle screws inserted to 20 mm depth)

| Pedicle Screw | OD | Mean (N) | SD (N) |
|---|---|---|---|
| Pedicle Screw 600 | 6.5 | 1180.90 | 82.88 |
| Competitor 1 | 6.5 | 1042.87 | 40.80 |
| Competitor 2 | 7.0 | 1017.28 | 54.66 |
| Taper Lock Screw | 6.5 | 957.64 | 33.22 |
| Set Screw | 6.5 | 949.76 | 53.00 |
| Competitor 6 | 6.5 | 943.47 | 35.20 |
| Competitor 3 | 6.0 | 930.00 | 27.68 |
| Competitor 4 | 6.5 | 898.75 | 33.12 |
| Competitor 5 | 6.5 | 892.01 | 38.46 |
| Competitor 7 | 5.5 | 649.65 | 22.11 |
| Competitor 8 | 5.0 | 578.48 | 16.71 |
| Competitor 9 | 5.5 | 571.37 | 12.82 |

As appreciated from the data provided in Tables 1 and 2, reproduced above, the features of the threaded buttress form arrangement and the tapering of both the major and minor diameter of bone screw member 620 provide an increase in pullout strength of the pedicle screw 600. Notably, since the leading third of the bone screw member 620 may have a smaller diameter than the trailing two-thirds of the bone screw member 620, the thread of the leading third of the bone screw member 620 creates an initial pathway while being inserted. As the bone screw member 620 is advanced distally into bone, the thread of the trailing two-thirds of the bone screw member 620 creates a new pathway in the bone that is larger in diameter than the initial pathway to achieve greater bone purchase.

The tapered shape of the leading third of the bone screw member 620 helps to wedge the bone screw member 620 into position within the bone while increasing the pullout strength. The thread may include a cutting flute that may be coincident with the distal tip of the screw to aid with insertion by making it easier to penetrate the bone and clear a pathway for trailing portions of the bone screw member 620. In embodiments, the cutting flute may be 0.025 inches wide with a 0.50 inch radius that is centered 0.525 inches off of the center axis (e.g., off of the thread or shank axis).

In general, when the pitch of a thread on a bone screw increases, more torque may be required to insert the bone screw, whereas, when the pitch of a thread on a bone screw decreases, it becomes more challenging to manufacture the bone screw. More particularly, as the pitch decreases and the lead is correspondingly decreased, another real disadvantage is that the number of rotations to achieve full insertion is increased since the screw travels a shorter axial distance with each revolution. Notably, the pitch of the thread of the bone screw member 620 provides an optimal balance between limiting the amount of torque required to insert the bone screw member 620 into bone and facilitating the manufacturing efficiencies necessary to optimize the performance of the screw. In embodiments, the pitch of the thread of the bone screw member 620 may be 0.079 inches (2 mm). The bone screw member 620 may have a double lead thread with the lead being 0.157 inches (4 mm) to aid in reducing the number of rotations it requires to insert the screw.

Turning now to FIGS. 25-28, a rod reducer 700 includes an outer member 710, an inner member 720, and a pair of gripping members 730. Outer member 710 includes a proximal segment 71, a distal segment 714, and a ring member 716 that is disposed between proximal and distal segments 712, 714. Proximal segment 712 includes an engaging portion 712a at a distal end of proximal segment 712 and a gripping portion 712b at a proximal end of proximal segment 712. An inner surface 712c of proximal segment 712 is threaded. Distal segment 714 defines a slot 714c therethrough and includes a reducing portion 714a at a distal end of distal segment 714 and a receiving portion 714d at a proximal end of distal segment 714. Receiving portion 714d includes a plurality of gripping features 715 on an outer surface of receiving portion 714d. A pair of rod engaging slots 714b and a pair of gripping member receiving slots 714e are defined through reducing portion 714a. Receiving portion 714d of distal segment 714 is configured to receive engaging portion 712a of proximal segment 712 so that ring member 716 is disposed between proximal and distal segments 712, 714. The components of outer member 710 may be integrally formed or assembled.

Inner member 720 includes an elongate body member 722 that defines an annular recess 728 configured to receive the pair of gripping members 730 so that the gripping members 730 are disposed in opposition on the elongate body member 722. Inner member 720 member 722 includes a pair of arms 726 supported on a distal end of elongate body member 722. A proximal end of elongate body member 722 has a threaded arrangement 724 that mates with threaded inner surface 712c of proximal segment 712 of outer member 712 to axially advance outer member 712 relative to inner member 720 as will be described in greater detail below.

Each gripping member 730 includes a body 732 having a supporting member 734, a proximal finger 738, and a distal finger 736. Supporting member 734 is configured to engage annular recess 728 of inner member 720 to support body 732 of each gripping member 730 on inner member 720. Proximal finger 738 extends proximally from supporting member 734 and is slidably positionable within slot 714c of outer member 710. Distal finger 736 extends distally from supporting member 734 and is positionable between an arm 726 of inner member 720 and reducing portion 714a of outer member 710 so that distal finger 736 is substantially aligned with a gripping member receiving slot 714e of reducing portion 714a.

As illustrated in FIGS. 29A-29C, with outer member 710 of rod reducer 700 disposed in a proximal position relative inner member 720 of rod reducer 700, distal fingers 736 of gripping member 730 of rod reducer 700 are secured to an outer surface of an embodiment of a polyaxial pedicle screw, for example, polyaxial pedicle screw 900. Proximal segment 712 of outer member 710 may then be rotated by virtue of the threaded arrangement between outer member 710 and inner member 720 to axially advance distal segment 714 of outer member 710 relative to inner member 720 and proximal segment 712. Proximal segment 712 remains axially fixed when rotated. Notably, as proximal segment 712 rotates, distal segment 714 remains radially fixed as distal segment 714 axially translates relative to inner member 720 and proximal segment 712. Outer member 710 approximates a spinal rod 800 positioned between rod reducer 700 and pedicle screw 900 as outer member 710 is advanced toward pedicle screw 900 to secure spinal rod 800 within a saddle of pedicle screw 900. As outer member 710 advances distally, a proximal end of slot 714c of outer member 710 approximates a proximal end of proximal fingers 738 of gripping member 730.

Turning now to FIGS. 30-31, a rod reducer and handle assembly 1000 includes the rod reducer 700 and a handle assembly 1002. Handle assembly 1002 includes a turning handle 1200 and an anti-torque handle 1100 that are selectively connectable to gripping portion 712b of rod reducer 700. Turning handle 1200 includes a shaft 1210, a handle 1220, and a socket 1230 that defines an opening 1232. Opening 1232 is configured to receive a proximal end of gripping portion 712b of rod reducer 700. Handle 1220 is secured to a proximal end of shaft 1210 and socket 1230 is secured to a distal end of shaft 1210. Anti-torque handle 1100 includes a shaft 1120 and a handle 1110 that may be integrally formed. Shaft 1120 includes a socket 1122 that defines an opening 1122a at a distal end of socket 112. Opening 1122a is disposed in communication with a lumen 1125 defined within shaft 1120 and another opening 1124 disposed at a proximal end of shaft 1120 so that anti-torque handle 1100 may slide over gripping portion 712b of rod reducer 700 and engage with gripping feature 715 of rod reducer 700 to prevent rotational movement of distal segment 714 of outer member 714 of rod reducer 700.

Thus, if needed, either or both turning handle 1200 and anti-torque handle 1100 may be used to facilitate the rotational movement of outer member 710 relative to inner member 720. In particular, rotation of turning handle 1200 imparts rotational movement to proximal segment 712 of outer member 710 and anti-torque handle 1100 imparts counter rotational movement to distal segment 714 of outer member 710 so that proximal segment 712 rotates and distal segment 714 axially translates without rotating. As appreciated, anti-torque handle 1100 is configured to limit the amount of torque imparted from the rotational movement imparted by turning handle 1200 to prevent undesirable torquing of the outer member 710. More particularly, anti-torque handle 1100 slides down over the outer surface of outer member 710 of rod reducer 700 so that a distal end of anti-torque handle 1100 engages distal segment 714 of outer member 710 and a proximal end of proximal segment 712 of outer member 710 is exposed for engagement with turning handle 1200. Meanwhile, since gripping member 730 is secured within annular recess 728 of inner member 720 such that proximal finger 738 of gripping member 730 is supported in slot 714c of distal segment 714 of outer member 710, the engagement of anti-torque handle 1110 with gripping feature 715 of distal segment 714 of outer member 710 prevents rotation of both distal segment 714 of outer member 710 and inner member 720 as proximal segment 712 of outer member 710 is rotated with turning handle 1200. After spinal rod 800 is fully reduced into the saddle of one of the presently disclosed pedicle screws, for example, pedicle screw 900, turning handle 1200 and anti-torque handle] 100 may be removed and a set screw may be inserted down an inner diameter of rod reducer 700 to lock spinal rod 800 into place. Alternatively, anti-torque handle 1100 may also be used to prevent rotation when tightening the set screw after spinal rod 800 has been fully reduced. Rod reducer 700 may then be removed. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A polyaxial pedicle screw comprising:
   a bone screw member having a head and a threaded shaft extending from the head along a shaft axis; and
   a housing positionable on the head of the bone screw member, the housing extending along a longitudinal axis between a proximal portion and a distal portion, the proximal portion having a channel adapted to receive a spinal rod therein in an orientation transverse to the longitudinal axis, and the distal portion defining a distal opening,
   wherein the head of the bone screw member is shaped such that the head defines a first outer profile along a plane perpendicular to the longitudinal axis when the bone screw member is in a first orientation, in which the shaft axis defines a first angle with respect to the longitudinal axis, and wherein the head of the bone screw member defines a second outer profile along the plane perpendicular to the longitudinal axis when the bone screw member is in a second orientation, in which the shaft axis defines a second angle with respect to the longitudinal axis, the second angle being different from the first angle, wherein the first outer profile is shaped to be receivable through the distal opening of the housing when the bone screw member is in the first orientation, and wherein the second outer profile is shaped to prevent the head from passing through the distal opening when the bone screw member is in the second orientation.

2. The polyaxial pedicle screw of claim 1, wherein the distal opening of the housing and the first outer profile of the head of the bone screw member have circular shapes, with a diameter of the first outer profile being smaller than a diameter of the distal opening.

3. The polyaxial pedicle screw of claim 1, wherein the distal opening of the housing and the first outer profile of the head of the bone screw member have circular shapes, with a diameter of the second outer profile being larger than a diameter of the distal opening.

4. The polyaxial pedicle screw of claim 1, wherein the first angle of the first orientation of the bone screw member is substantially 90°, and wherein the second angle of the second orientation of the bone screw member is substantially 180°.

5. The polyaxial pedicle screw of claim 1, wherein the head of the bone screw member has a substantially spherical shape with a cylindrical portion formed therein, such that the first outer profile is defined by the cylindrical portion.

6. The polyaxial pedicle screw of claim 1, wherein the housing includes a recess positioned to receive a portion of the threaded shaft of the bone screw member when the first outer profile of the head of the bone screw member is received through the distal opening of the housing in the first orientation.

7. The polyaxial pedicle screw of claim 6, wherein the housing includes a collar extending from the distal portion of the housing, the collar defining the recess therein, and wherein the portion of the threaded shaft of the bone screw member receivable in the recess is a neck of the threaded shaft disposed between the head and a threaded portion of the threaded shaft.

8. The polyaxial pedicle screw of claim 6, further comprising a cap securable to the housing so as to cover the recess.

9. The polyaxial pedicle screw of claim 1, further comprising an anvil positionable within the housing adjacent to the head of the bone screw member when the anvil and the head of the bone screw member are positioned within the housing, the anvil defining a groove in an outer surface thereof, the groove defining a flap, the flap extending over the groove and being flexibly attached to the anvil to enable the anvil to flex an amount sufficient to maintain the head of the bone screw member in constant contact with the anvil.

10. The polyaxial pedicle screw of claim 9, wherein the anvil defines a cavity having a surface with a plurality of radii of curvature to accommodate variously sized rod members.

11. The polyaxial pedicle screw of claim 10, wherein the surface of the cavity defines a first section with a first radius of curvature, a second section with a second radius of curvature, and a third section with a third radius of curvature, such that the plurality of radii of curvature define a compound curve that provides at least two lines of contact on a plurality of different diameter rod members.

12. The polyaxial pedicle screw of claim 9, wherein, when the anvil is positioned within the housing, the outer surface of the anvil defines a non-circular shape in a cross sectional plane extending orthogonal to the longitudinal axis of the housing, so as to prevent the anvil from rotating with respect to the housing about the longitudinal axis.

13. The polyaxial pedicle screw of claim 12, wherein the non-circular shape is defined by a protuberance on the outer surface of the anvil, and wherein the housing defines a slot on an inner surface thereof, the protuberance and the slot being engageable to prevent the anvil from rotating with respect to the housing about the longitudinal axis.

14. The polyaxial pedicle screw of claim 1, further comprising a cap securable to the housing to prevent the bone screw member from reorienting to the first orientation.

15. The polyaxial pedicle screw of claim 1, wherein the first outer profile of the head of the bone screw member is defined by a portion of the head having a roughened surface texture, and wherein the second outer profile of the head of the bone screw member is defined by a portion of the head having a smooth surface.

16. A polyaxial pedicle screw comprising:
a bone screw member having a head and a threaded shaft extending from the head along a shaft axis, the head including a first outer surface region having a partially spherical shape defined by a first radius of curvature, and the head including a second outer surface region having a partially cylindrical shape defined by a second radius of curvature from a center of curvature defined along an axis of the partially cylindrical shape, the axis of the partially cylindrical shape extending transverse to the shaft axis, and the second radius of curvature being smaller than the first radius of curvature; and
a housing extending along a longitudinal axis between a proximal portion and a distal portion, the proximal portion having a channel adapted to receive a spinal rod therein in an orientation transverse to the longitudinal axis, and the distal portion defining a distal opening configured to receive the head of the bone screw member therethrough.

17. The polyaxial pedicle screw of claim 16, wherein the distal opening of the housing has a circular shape defined by a radius that is larger than the second radius of curvature and smaller than the first radius of curvature.

18. The polyaxial pedicle screw of claim 16, wherein the first outer surface region of the head of the bone screw member has a roughened surface texture, and wherein the second outer surface region of the head of the bone screw member has a smooth surface.

* * * * *